(12) United States Patent
Nakatsu et al.

(10) Patent No.: US 11,667,620 B2
(45) Date of Patent: Jun. 6, 2023

(54) COMPOSITION, FILM, FILM-FORMING METHOD AND PATTERNED SUBSTRATE-PRODUCING METHOD

(71) Applicant: JSR CORPORATION, Tokyo (JP)

(72) Inventors: Hiroki Nakatsu, Tokyo (JP); Kazunori Takanashi, Tokyo (JP); Kazunori Sakai, Tokyo (JP); Yuushi Matsumura, Tokyo (JP); Hiroki Nakagawa, Tokyo (JP)

(73) Assignee: JSR CORPORATION, Tokyo (JP)

(*) Notice: Subject to any disclaimer, the term of this patent is extended or adjusted under 35 U.S.C. 154(b) by 523 days.

(21) Appl. No.: 16/809,740

(22) Filed: Mar. 5, 2020

(65) Prior Publication Data
US 2020/0199093 A1    Jun. 25, 2020

Related U.S. Application Data

(63) Continuation of application No. PCT/JP2018/032434, filed on Aug. 31, 2018.

(30) Foreign Application Priority Data

Sep. 7, 2017 (JP) .............................. JP2017-172559

(51) Int. Cl.
| | | |
|---|---|---|
| C07D 317/64 | (2006.01) |
| G03F 7/11 | (2006.01) |
| G03F 7/16 | (2006.01) |
| C07D 405/14 | (2006.01) |
| C09D 201/06 | (2006.01) |
| G03F 7/20 | (2006.01) |
| G03F 7/32 | (2006.01) |
| G03F 7/38 | (2006.01) |

(52) U.S. Cl.
CPC ......... *C07D 317/64* (2013.01); *C07D 405/14* (2013.01); *C09D 201/06* (2013.01); *G03F 7/11* (2013.01); *G03F 7/162* (2013.01); *G03F 7/168* (2013.01); *G03F 7/2006* (2013.01); *G03F 7/322* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 9,075,309 B2 | 7/2015 | Ogihara et al. | |
| 9,746,768 B2 | 8/2017 | Ohnishi | |
| 10,234,762 B2 | 3/2019 | Ishikawa | |
| 2012/0108043 A1 | 5/2012 | Hatakeyama | |
| 2013/0045601 A1 | 2/2013 | Og | |
| 2013/0210236 A1* | 8/2013 | Ogihara | C09D 183/06 430/286.1 |
| 2015/0362835 A1 | 12/2015 | Ohnishi | |
| 2017/0003592 A1 | 1/2017 | Ishikawa | |

FOREIGN PATENT DOCUMENTS

| | | | |
|---|---|---|---|
| JP | 2001215727 A | * | 8/2001 |
| JP | 2004177668 A | | 6/2004 |
| JP | 3601548 B2 | * | 12/2004 |
| JP | 2011068888 A | * | 4/2011 |
| JP | 2012098520 A | | 5/2012 |
| JP | 2013041140 A | | 2/2013 |
| JP | 2013167669 A | | 8/2013 |
| JP | 2017092433 A | | 5/2017 |
| TW | 201336857 A | | 9/2013 |
| WO | WO-2014/115843 A1 | | 7/2014 |
| WO | WO-2015/146524 A1 | | 10/2015 |

OTHER PUBLICATIONS

English Machine Translation of JP2011068888A (Year: 2011).*
English Machine Translation of JP2001215727A (Year: 2001).*
Office Action dated Jan 4. 2022 in Japanese Patent Application No. 2019-540935 (with English translation), 10 pages.
International Search Report dated Nov. 13, 2018 in PCT Application No. PCT/JP2018/032434 (with English translation).
Written Opinion dated Nov. 13, 2018 in PCT Application No. PCT/JP2018/032434 (with English translation).
Combined Office Action and Search Report dated Dec. 27, 2021 in Taiwanese Patent Application No. 107130835 (with English translation), 16 pages.
Office Action dated Dec. 1, 2022 in Korean Patent Application No. 10-2020-7006383 (with English translation), 8 pages.

* cited by examiner

*Primary Examiner* — Duane Smith
*Assistant Examiner* — Nicholas E Brown
(74) *Attorney, Agent, or Firm* — Element IP, PLC

(57) ABSTRACT

The composition contains a compound and a solvent. The compound includes a group represented by formula (1). The compound has a molecular weight of no less than 200 and has a percentage content of carbon atoms of no less than 40% by mass. In the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond; $Ar^1$ represents a group obtained by removing (n+3) hydrogen atoms from an arene or heteroarene having 6 to 20 ring atoms; and X represents an oxygen atom, $-CR^3R^4-$, $-CR^3R^4-O-$ or $-O-CR^3R^4-$.

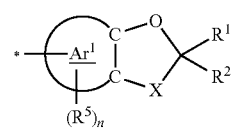

(1)

18 Claims, 1 Drawing Sheet

COMPOSITION, FILM, FILM-FORMING METHOD AND PATTERNED SUBSTRATE-PRODUCING METHOD

CROSS-REFERENCE TO RELATED APPLICATIONS

The present application is a continuation application of International Application No. PCT/JP2018/032434, filed Aug. 31, 2018, which claims priority to Japanese Patent Application No. 2017-172559, filed Sep. 7, 2017. The contents of these applications are incorporated herein by reference in their entirety.

BACKGROUND OF THE INVENTION

Field of the Invention

The present invention relates to a composition, a film, a film-forming method, and a patterned substrate-producing method.

Description of the Related Art

In manufacturing semiconductor devices, multilayer resist processes have been employed for attaining a high degree of integration. In these processes, a composition for forming a resist underlayer film is first applied directly or indirectly on at least an upper face side of a substrate, and then a coating film thus obtained is heated, thereby forming a resist underlayer film. A resist pattern is formed by using a resist composition directly or indirectly on an upper face side of the resist underlayer film. Subsequently, the resist underlayer film is etched by using the resist pattern as a mask, and further, the substrate is etched by using the resultant resist underlayer film pattern as a mask, thereby enabling a desired pattern to be formed on the substrate. Accordingly, a patterned substrate can be obtained. The resist underlayer film for use in such a multilayer resist process is required to have general characteristics such as solvent resistance.

Furthermore, recently, there are increasing cases of pattern formation on a substrate having multiple types of trenches, particularly trenches with aspect ratios that are different from one another. In these cases, the composition for resist underlayer film formation is required to sufficiently fill these trenches and to be capable of forming a film having superior flatness. To meet these demands, structures of polymers, etc. contained in the composition for resist underlayer film formation, and functional groups included in the polymers have been extensively investigated (see Japanese Unexamined Patent Application, Publication No. 2004-177668).

Moreover, in practical manufacture of semiconductor devices, there exist cases in which reprocessing is to be conducted when a silicon-containing film is formed on a substrate or when defects are generated upon patterning of a resist film. For a case in which a film to be removed is a silicon-containing film in the reprocessing, subjecting to a wet peeling treatment with a basic liquid has been proposed as a removing procedure of the silicon-containing film (see, PCT International Publication No. 2015/146524 and Japanese Unexamined Patent Application, Publication No. 2017-92433). In this case, if a resist underlayer film is present between a substrate and the silicon-containing film, the resist underlayer film is required to have wet peel resistance against the basic liquid.

Additionally, along with progress in microfabrication of a substrate pattern to be formed, recently, the resist underlayer film has also been required to be superior in flexural resistance to be accompanied by less bending when the substrate is etched using a formed underlayer film pattern as a mask.

SUMMARY OF THE INVENTION

According to an aspect of the present invention, a composition includes a compound and a solvent. The compound includes a group represented by formula (1). The compound has a molecular weight of no less than 200 and has a percentage content of carbon atoms of no less than 40% by mass.

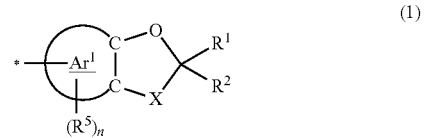

(1)

In the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond; $Ar^1$ represents a group obtained by removing (n+3) hydrogen atoms from an arene or heteroarene having 6 to 20 ring atoms; X represents an oxygen atom, $-CR^3R^4-$, $-CR^3R^4-O-$ or $-O-CR^3R^4-$, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond; n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and * denotes a binding site to a part other than the group represented by the formula (1) in the compound.

According to another aspect of the present invention, a film is formed from the composition.

According to further aspect of the present invention, a film-forming method includes applying the composition directly or indirectly on at least an upper face side of a substrate to form a coating film. The coating film is heated.

According to further aspect of the present invention, a patterned substrate-producing method includes applying a composition directly or indirectly on at least an upper face side of a substrate to form a coating film. The coating film is heated to form a film. A silicon-containing film is formed on an upper face side of the film formed by the heating. The silicon-containing film is removed with a basic liquid. The composition includes a compound and a solvent. The compound includes a group represented by formula (1). The compound has a molecular weight of no less than 200 and has a percentage content of carbon atoms of no less than 40% by mass.

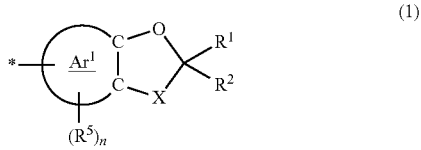

In the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond; $Ar^1$ represents a group obtained by removing (n+3) hydrogen atoms from an arene or heteroarene having 6 to 20 ring atoms; X represents an oxygen atom, $-CR^3R^4-$, $-CR^3R^4-O-$ or $-O-CR^3R^4-$, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond; n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and * denotes a binding site to a part other than the group represented by the formula (1) in the compound.

According to further aspect of the present invention, a patterned substrate-producing method includes applying a composition directly or indirectly on at least an upper face side of a substrate to form a coating film. The coating film is heated to form a film. A silicon-containing film is formed on an upper face side of the film formed by the heating. A resist pattern is formed on an upper face sided of the silicon-containing film. The substrate is etched using the resist pattern as a mask. The composition includes a compound and a solvent. The compound includes a group represented by formula (1). The compound has a molecular weight of no less than 200 and has a percentage content of carbon atoms of no less than 40% by mass.

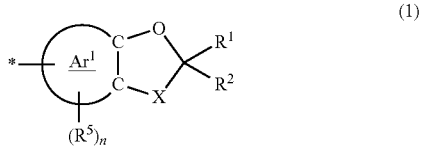

In the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond; $Ar^1$ represents a group obtained by removing (n+3) hydrogen atoms from an arene or heteroarene having 6 to 20 ring atoms; X represents an oxygen atom, $-CR^3R^4-$, $-CR^3R^4-O-$ or $-O-CR^3R^4-$, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond; n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and * denotes a binding site to a part other than the group represented by the formula (1) in the compound.

DESCRIPTION OF EMBODIMENTS

Figure 1:
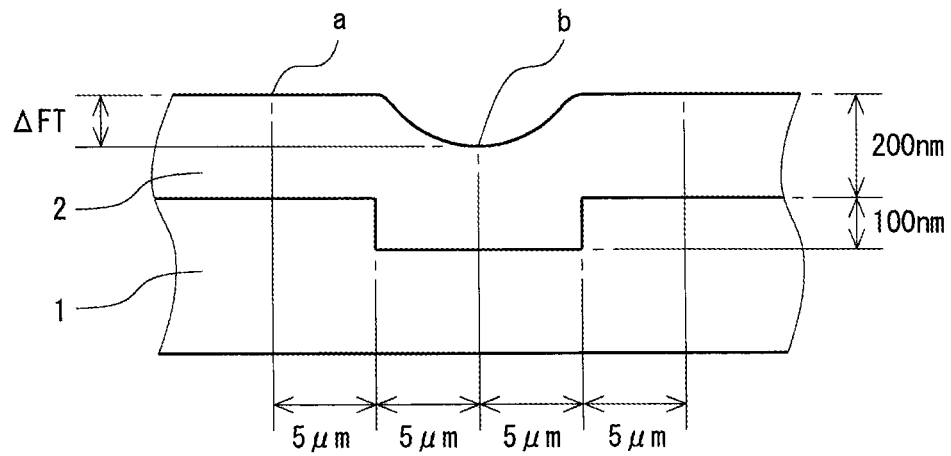
FIG. 1 is a schematic cross-sectional view for illustrating an evaluation method of flatness.

According to one embodiment of the invention, a composition contains: a compound (hereinafter, may be also referred to as "(A) compound" or "compound (A)") including a group represented by the following formula (1) (hereinafter, may be also referred to as "group (I)"), the compound (A) having a molecular weight of no less than 200, and having a percentage content of carbon atoms of no less than 40% by mass; and a solvent (hereinafter, may be also referred to as "(B) solvent" or "solvent (B)"),

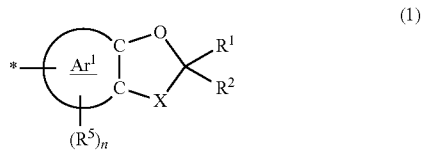

wherein, in the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;

$Ar^1$ represents a group obtained by removing (n+3) hydrogen atoms from an arene or heteroarene having 6 to 20 ring atoms;

X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond;

n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with the atom chain to which the two or more of the plurality of $R^5$s bond and

* denotes a binding site to a part other than the group represented by the above formula (1) in the compound (A).

According to another embodiment of the invention, a film is formed from the composition of the embodiment of the invention.

According to a further embodiment of the invention, a film-forming method (hereinafter, may be also referred to as "film-forming method (I)") includes:

a step of applying a composition directly or indirectly on at least an upper face side of a substrate to form a coating film, the composition containing the compound (A) and the solvent (B) (hereinafter, may be also referred to as "applying step (I)"); and a step of heating the coating film formed by the applying step (I) (hereinafter, may be also referred to as "heating step (I)").

According to still another embodiment of the invention, a film-forming method (hereinafter, may be also referred to as "film-forming method (II)") includes:

a step of applying a composition directly or indirectly on at least an upper face side of a substrate to form a coating film, the composition containing the compound (A) and the solvent (B) (hereinafter, may be also referred to as "applying step (II)"); and a step of heating the coating film formed by the applying step (I) at a temperature of no less than 300° C. (hereinafter, may be also referred to as "heating step (II)").

According to a still further embodiment of the invention, a patterned substrate-producing method (hereinafter, may be also referred to as "patterned substrate-producing method (I)") includes:

a step of applying a composition directly or indirectly on at least an upper face side of a substrate to form a coating film, the composition containing the compound (A) and the solvent (B) (hereinafter, may be also referred to as "applying step (III)");

a step of heating the coating film formed by the applying step (III) to form a film (hereinafter, may be also referred to as "heating step (III)");

a step of forming a silicon-containing film on an upper face side of the film formed by the heating step (III) (hereinafter, may be also referred to as "silicon-containing film-forming step (I)"); and a step of removing the silicon-containing film with a basic liquid (hereinafter, may be also referred to as "silicon-containing film-removing step").

According to yet another embodiment of the invention, a patterned substrate-producing method (hereinafter, may be also referred to as "patterned substrate-producing method (II)") includes:

a step of applying a composition directly or indirectly on at least an upper face side of a substrate to form a coating film, the composition containing the compound (A) and the solvent (B) (hereinafter, may be also referred to as "applying step (IV)");

a step of heating the coating film formed by the applying step (IV) to form a film (hereinafter, may be also referred to as "heating step (IV)");

a step of forming a silicon-containing film on an upper face side of the film formed by the heating step (IV) (hereinafter, may be also referred to as "silicon-containing film-forming step (II)");

a step of forming a resist pattern on an upper face side of the silicon-containing film (hereinafter, may be also referred to as "resist pattern-forming step (II)"); and a step of etching the substrate using the resist pattern as a mask (hereinafter, may be also referred to as "etching step (II)").

The composition of the embodiment of the present invention enables formation of a film that is superior in flatness, wet peel resistance, and flexural resistance of a pattern, with solvent resistance being maintained. The film of the embodiment of the present invention is superior in flatness, wet peel resistance, and flexural resistance of a pattern, with solvent resistance being maintained. The film-forming method of the embodiment of the present invention enables formation of a film that is superior in flatness, wet peel resistance, and flexural resistance of a pattern, with solvent resistance being maintained. The patterned substrate-producing method of the embodiment of the present invention enables a favorable patterned substrate to be obtained by using a superior film formed as described above. Therefore, these can be suitably used for manufacture, etc., of semiconductor devices in which further progress of microfabrication is expected in the future. Hereinafter, the embodiments of the present invention will be described in detail.

Composition

The composition of one embodiment of the present invention contains the compound (A) and the solvent (B). The composition may contain optional component(s) within a range not leading to impairment of the effects of the present invention. Each component will be described in the following.

(A) Compound

The compound (A) includes the group (I), and has a molecular weight of no less than 200 and a percentage content of carbon atoms of no less than 40% by mass. The compound (A) may have one group (I), or may have two or more groups (I). One, or two or more types of the compound (A) may be used.

Due to containing the compound (A), the composition enables formation of a film that is superior in flatness, wet peel resistance, and flexural resistance of a pattern, with solvent resistance being maintained. Although not necessarily clarified and without wishing to be bound by any theory, the reason for achieving the effects described above due to the aforementioned constitution in the composition may be supposed as in the following, for example. Specifically, it is considered that crosslinking of the compound (A) does not occur, and accordingly hardening does not occur, unless the compound (A) is exposed to a comparatively high temperature, and a state of high fluidity of the composition can thus be maintained until the hardening occurs. Therefore, a film to be formed is believed to have improved flatness. In addition, the compound (A) has a structure in which a —$CR^1R^2$— group is adjacent to an oxygen atom bonding to a ring of an arene or heteroarene in the group which may be represented by $Ar^1$. This structure is less likely to undergo oxidative degradation, comparatively, even in a case of being heated at a high temperature. Therefore, it is believed that production of phenolic hydroxyl groups is inhibited in the film to be formed, and consequently wet peel resistance against a basic liquid may be improved. Furthermore, due to having the structure described above, the compound (A) is considered to have appropriately enhanced strength, whereby flexural resistance of a pattern may be improved.

Group (I)

The group (I) is represented by the following formula (1).

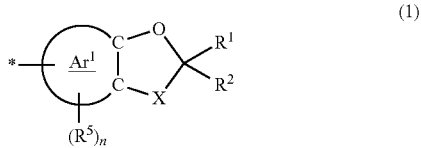

(1)

In the above formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;

$Ar^1$ represents a group obtained by removing (n+3) hydrogen atoms from an arene or heteroarene having 6 to 20 ring atoms;

X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond;

n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with the atom chain to which the two or more of the plurality of $R^5$s bond and

* denotes a binding site to a part other than the group (I) in the compound (A). It is to be noted that the "organic group" as referred to herein means a group that includes at least one carbon atom.

Examples of the monovalent hydrocarbon group having 1 to 20 carbon atoms which may be represented by $R^1$ to $R^4$ include: chain hydrocarbon groups, e.g., alkyl groups such as a methyl group, an ethyl group, a propyl group, a butyl group and a pentyl group, alkenyl groups such as an ethenyl group, a propenyl group and a butenyl group, and alkynyl groups such as an ethynyl group, a propynyl group and a butynyl group; alicyclic hydrocarbon groups, e.g., cycloalkyl groups such as a cyclopentyl group and a cyclohexyl group, cycloalkenyl groups such as a cyclopropenyl group, a cyclopentenyl group and a cyclohexenyl group, and bridged cyclic hydrocarbon groups such as a norbornyl group and an adamantyl group; aromatic hydrocarbon groups, e.g., aryl groups such as a phenyl group, a tolyl group, a xylyl group and a naphthyl group, and aralkyl groups such as a benzyl group, a phenethyl group and a naphthylmethyl group; and the like.

The monovalent fluorinated hydrocarbon group having 1 to 20 carbon atoms which may be represented by $R^1$ to $R^4$ is exemplified by a group obtained by substituting with a fluorine atom a part or all of hydrogen atoms included in the monovalent hydrocarbon group which may be represented by $R^1$ to $R^4$ described above, and the like.

Examples of the ring structure having 3 to 20 ring atoms which may be constituted by groups represented by $R^1$ to $R^4$ include: cycloalkane structures such as a cyclopropane structure, a cyclopentane structure and a cyclohexane structure; bridged structures such as a norbornane structure and an adamantane structure; and the like.

$R^1$ and $R^2$ each represent preferably a hydrogen atom, a fluorine atom or an alkyl group.

Examples of the arene having 6 to 20 ring atoms that gives $Ar^1$ include benzene, naphthalene, anthracene, phenanthrene, tetracene, pyrene, triphenylene, perylene, and the like. Of these, benzene or naphthalene is preferred, and benzene is more preferred.

Examples of the heteroarene having 6 to 20 ring atoms that gives $Ar^1$ include pyridine, quinoline, isoquinoline, indole, pyran, benzopyran, benzofuran, benzothiophene, and the like.

The oxygen atom and the group represented by X which may bond to $Ar^1$ in the above formula (1) each bond to carbon atoms adjacent thereto in the aromatic ring of $Ar^1$.

X represents preferably an oxygen atom or —$CR^3R^4$—O—, and more preferably an oxygen atom.

$R^3$ and $R^4$ each represent preferably a hydrogen atom.

The monovalent organic group having 1 to 20 carbon atoms which may be represented by $R^5$ is exemplified by: a monovalent hydrocarbon group having 1 to 20 carbon atoms; a group (a) that includes a divalent hetero atom-containing group between two adjacent carbon atoms of this hydrocarbon group, or between this hydrocarbon group and an atom to which $R^5$ bonds; a group obtained by substituting with a monovalent hetero atom-containing group, a part or all of hydrogen atoms included in the aforementioned hydrocarbon group or the group (a); and the like.

Examples of the monovalent hydrocarbon group having 1 to 20 carbon atoms include groups similar to the monovalent hydrocarbon groups having 1 to 20 carbon atoms which may be represented by $R^1$ to $R^4$ described above, and the like.

Examples of the divalent hetero atom-containing group include —CO—, —CS—, —NH—, —O—, —S—, a combination thereof, and the like.

Examples of the group (a) that includes a divalent hetero atom-containing group between two adjacent carbon atoms of a hydrocarbon group, or between the hydrocarbon group and an atom to which $R^5$ bonds include:

hetero atom-containing chain groups such as an oxoalkyl group, a thioalkyl group, an alkylaminoalkyl group, an alkoxyalkyl group and an alkylthio alkyl group;

hetero atom-substituted alicyclic groups such as an oxocycloalkyl group and a thiocycloalkyl group;

aliphatic heterocyclic groups such as an azacycloalkyl group, an oxacycloalkyl group, a thiacycloalkyl group, an oxocycloalkenyl group and an oxathiacycloalkyl group;

aromatic heterocyclic groups, e.g., heteroaryl groups such as a pyrrolyl group, a pyridyl group, a quinolyl group, an isoquinolyl group, a furyl group, a pyranyl group, a thienyl group and a benzothiophenyl group; and the like.

Examples of the monovalent hetero atom-containing group include a hydroxy group, a sulfanyl group, a cyano group, a nitro group, a halogen atom, and the like.

In the above formula (1), n is preferably 0 to 3, more preferably 0 to 2, still more preferably 0 or 1, and particularly preferably 0.

Examples of the ring structure having 4 to 20 ring atoms which may be constituted from two or more of the plurality of $R^5$s include: alicyclic structures such as a cyclohexane structure and a cyclohexene structure; aliphatic heterocyclic structures such as an azacyclohexane structure and an azacyclohexene structure; aromatic ring structures such as a benzene structure and a naphthalene structure; aromatic heterocyclic structures such as a pyridine structure; and the like.

The lower limit of the number of the group (I) included in the compound (A) is preferably 2, and more preferably 3. The upper limit of the number of the group (I) is preferably 6, and more preferably 5. When the number of the group (I) in the compound (A) falls within the above range, a degree of crosslinking in a film to be formed is increased, and thus a hardening character of the composition is further improved.

Examples of the compound (A) include a compound represented by the following formula (2) (hereinafter, may be also referred to as "compound (i)"), a resin (hereinafter, may be also referred to as "resin (i)"), and the like. The compound (i) and the resin (i) are described below in this order.

Compound (i)

The compound (i) is represented by the following formula (2).

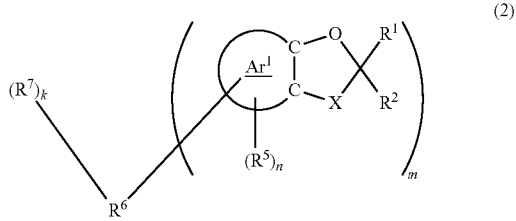

(2)

In the above formula (2), $R^1$, $R^2$, $Ar^1$, X and n are as defined in the above formula (1), wherein in a case in which n is 0, $R^6$ represents an organic group having 1 to 60 carbon atoms and having a valency of (m+k), in a case in which n is 1, $R^5$ represents a hydroxy group, a halogen atom, a nitro group or a monovalent organic group having 1 to 20 carbon atoms and $R^6$ represents an organic group having 1 to 60 carbon atoms and having a valency of (m+k), or $R^5$ and $R^6$ taken together represent a part of a ring structure having 4 to 20 ring atoms constituted together with the carbon chain to which $R^5$ and $R^6$ bond, and in a case in which n is no less than 2, a plurality of $R^5$s are identical or different from each other and each $R^5$ independently represent a hydroxy group, a halogen atom, a nitro group or a monovalent organic group having 1 to 20 carbon atoms and $R^6$ represents an organic group having 1 to 60 carbon atoms and having a valency of (m+k), or two or more of the plurality of $R^5$s taken together represent a part of a ring structure having 4 to 20 ring atoms constituted together with the atom chain to which the two or more of the plurality of $R^5$s bond, and $R^6$ represents an organic group having 1 to 60 carbon atoms and having a valency of (m+k), $R^6$ and or one or more of a plurality of $R^5$s taken together represent a part of a ring structure having 4 to 20 ring atoms constituted together with the carbon chain to which the $R^6$ and one or more of a plurality of $R^5$s bond; m is an integer of 1 to 10; $R^7$ represents a monovalent organic group having 1 to 20 carbon atoms; and k is an integer of 0 to 9, wherein (m+k) is no greater than 10, and wherein in a case in which m is no less than 2, a plurality of $R^1$s are identical or different from each other, a plurality of $R^1$s are identical or different from each other, a plurality of Xs are identical or different from each other, a plurality of $Ar^1$s are identical or different from each other and a plurality of n's are identical or different from each other, and in a case in which k is no less than 2, a plurality of $R^7$s are identical or different from each other.

The lower limit of m is preferably 2, and more preferably 3. The upper limit of m is preferably 8, and more preferably 6.

Examples of the monovalent organic group represented by $R^7$ include the group (I), wherein an —X—$CR^1R^2$—O— bond is not formed, and the like.

In the above formula (2), k is preferably 0 to 6, more preferably 0 to 2, still more preferably 0 or 1, and particularly preferably 0.

The lower limit of (m+k) is preferably 2, and more preferably 3. The upper limit of (m+k) is preferably 8, and more preferably 6.

The organic group having 1 to 60 carbon atoms and having a valency of (m+k) which may be represented by $R^6$ is exemplified by: a hydrocarbon group having 1 to 60 carbon atoms and having a valency of (m+k); a group (β) that includes a divalent hetero atom-containing group between two adjacent carbon atoms of this hydrocarbon group; a group obtained by substituting with a monovalent hetero atom-containing group, a part or all of hydrogen atoms included in the aforementioned hydrocarbon group or the group (β); and the like. $R^6$ is exemplified by a group obtained by removing (m+k−1) hydrogen atoms from the group exemplified as the monovalent organic group having 1 to 20 carbon atoms which may be represented by $R^5$, and the like.

$R^6$ represents preferably: an aliphatic hydrocarbon group having 2 to 20 carbon atoms; a group derived from an arene or heteroarene; a group having an aromatic ring and a carbon atom at a benzylic position bonding to the aromatic ring, the group being obtained by removing the hydrogen atom bonding to this carbon atom; a group derived from a lactone compound; or a group having 4 to 60 carbon atoms obtained by combining these groups. Any hydrogen atom of these groups in $R^6$ may be substituted with at least any one of a hydroxy group, a halogen atom, a nitro group and a cyano group.

Examples of the aliphatic hydrocarbon group having 2 to 20 carbon atoms include chain hydrocarbon groups and alicyclic hydrocarbon groups each having 2 to 20 carbon atoms, which are exemplified above as $R^1$ to $R^4$, and the like.

More specific examples of $R^6$ include groups (hereinafter, may be also referred to as "groups (1-1) to (1-6)") represented by the following formulae (1-1) to (1-6), and the like.

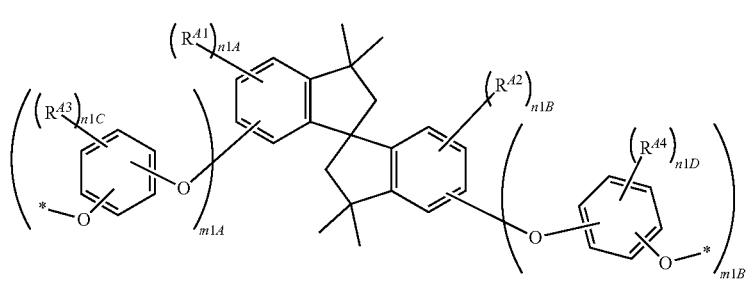
(1-1)

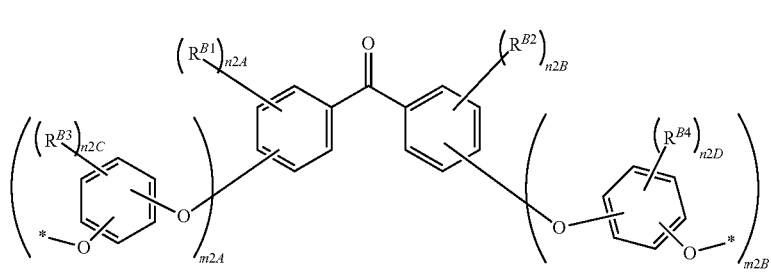
(1-2)

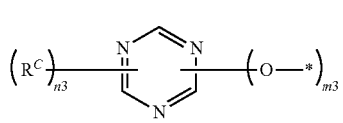
(1-3)

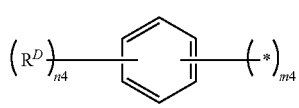
(1-4)

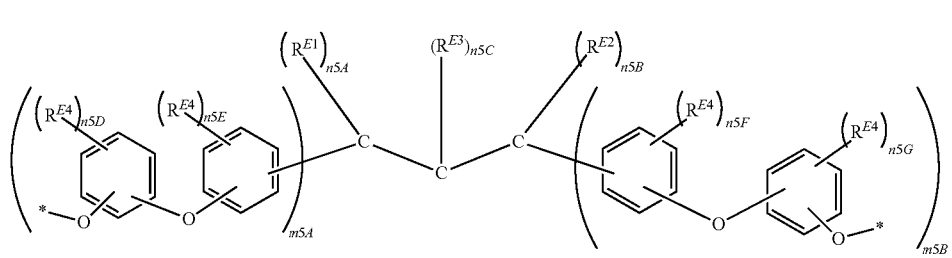
(1-5)

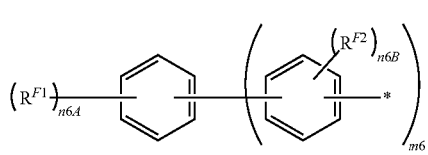
(1-6)

In the above formulae (1-1) to (1-6), * denotes a site that bonds to the carbon atom on the aromatic ring in $Ar^1$ in the above formula (2).

In the above formula (1-1), $R^{A1}$ to $R^{A4}$ each represent a hydroxy group, a halogen atom, a nitro group or a monovalent organic group having 1 to 20 carbon atoms; n1A and n1B are each an integer of 0 to 3; n1C and n1D are each an integer of 0 to 4; and m1A and m1B are each an integer of 1 to 4, wherein in a case in which n1A is no less than 2, a plurality of $R^{A1}$s are identical or different from each other, in a case in which n1B is no less than 2, a plurality of $R^{A2}$s are identical or different from each other, in a case in which n1C is no less than 2, a plurality of $R^{A3}$s are identical or different from each other, and in a case in which n1D is no less than 2, a plurality of $R^{A4}$s are identical or different from each other, and wherein (n1A+m1A)≤4, and (n1B+m1B)≤4. Each of n1A and n1B is preferably 0 or 1, and more preferably 0. Each of n1C and n1D is preferably 0 or 1. Each of m1A and m1B is preferably 1 or 2, and more preferably 2.

In the above formula (1-2), $R^{B1}$ to $R^{B4}$ each represent a hydroxy group, a halogen atom, a nitro group or a monovalent organic group having 1 to 20 carbon atoms; n2A, n2B, n2C and n2D are each an integer of 0 to 4; and m2A and m2B are each an integer of 1 to 5, wherein in a case in which n2A is no less than 2, a plurality of $R^{B1}$s are identical or different from each other, in a case in which n2B is no less than 2, a plurality of $R^{B2}$s are identical or different from each other, in a case in which n2C is no less than 2, a plurality of $R^{B3}$s are identical or different from each other, and in a case in which n2D is no less than 2, a plurality of $R^{B4}$s are identical or different from each other, and wherein (n2A+m2A)≤5, and (n2B+m2B)≤5. Each of n2A and n2B is preferably 0 or 1, and more preferably 0. Each of n2C and n2D is preferably 0 or 1. Each of m2A and m2B is preferably 2 or 3.

In the above formula (1-3), $R^C$ represents a hydroxy group, a halogen atom, a nitro group or a monovalent organic group having 1 to 20 carbon atoms; n3 is 0 or 1; and m3 is 2 or 3, wherein (n3+m3)≤3. In the above formula (1-3), n3 is preferably 0, and m3 is preferably 2 or 3.

In the above formula (1-4), $R^D$ represents a hydroxy group, a halogen atom, a nitro group or a monovalent organic group having 1 to 20 carbon atoms; n4 is an integer of 0 to 4; and m4 is an integer of 2 to 6, wherein in a case in which n4 is no less than 2, a plurality of $R^D$s are identical or different from each other, and wherein (n4+m4)≤6. In the above formula (1-4), n4 is preferably 0 or 1, and more preferably 0, whereas m4 is preferably 2, 3 or 4, and more preferably 3.

In the above formula (1-5), $R^{E1}$ to $R^{E7}$ each represent a hydroxy group, a halogen atom, a nitro group or a monovalent organic group having 1 to 20 carbon atoms; n5A, n5B and n5C are each an integer of 0 to 2; n5D, n5E, n5F and n5G are each an integer of 0 to 4; and m5A and m5B are each an integer of 1 to 3, wherein in a case in which n5A is 2, a plurality of $R^{E1}$s are identical or different from each other, in a case in which n5B is 2, a plurality of $R^{E2}$s are identical or different from each other, in a case in which n5C is 2, a plurality of $R^{E3}$s are identical or different from each other, in a case in which n5D is no less than 2, a plurality of $R^{E4}$s are identical or different from each other, in a case in which n5E is no less than 2, a plurality of $R^{E5}$s are identical or different from each other, in a case in which n5F is no less than 2, a plurality of $R^{E6}$s are identical or different from each other, and in a case in which n5G is no less than 2, a plurality of $R^{E7}$s are identical or different from each other, and wherein (n5A+m5A)≤3, and (n5B+m5B)≤3. Each of n5A, n5B and n5C is preferably 0 or 1, and more preferably 0. Each of n5D, n5E, n5F and n5G is preferably 0 or 1. Each of m5A and m5B is preferably 1 or 2.

In the above formula (1-6), $R^{F1}$ and $R^{F2}$ each represent a hydroxy group, a halogen atom, a nitro group or a monovalent organic group having 1 to 20 carbon atoms; n6A and n6B are each an integer of 0 to 4; and m6 is an integer of 2 to 6, wherein in a case in which n6A is no less than 2, a plurality of $R^{F1}$s are identical or different from each other, and in a case in which n6B is no less than 2, a plurality of $R^{F2}$s are identical or different from each other, and wherein (n6A+m6)≤6. In the above formula (1-6), n6A is preferably 0 or 1, and more preferably 0. Further, n6B is preferably 0 or 1, whereas m6 is preferably 2 or 3, and more preferably 3.

Examples of the monovalent organic group having 1 to 20 carbon atoms include groups similar to those exemplified in connection with $R^5$, and the like.

Examples of the compound (i) include compounds (hereinafter, may be also referred to as "compounds (i-1) to (i-7)") represented by the following formulae (i-1) to (i-7), and the like.

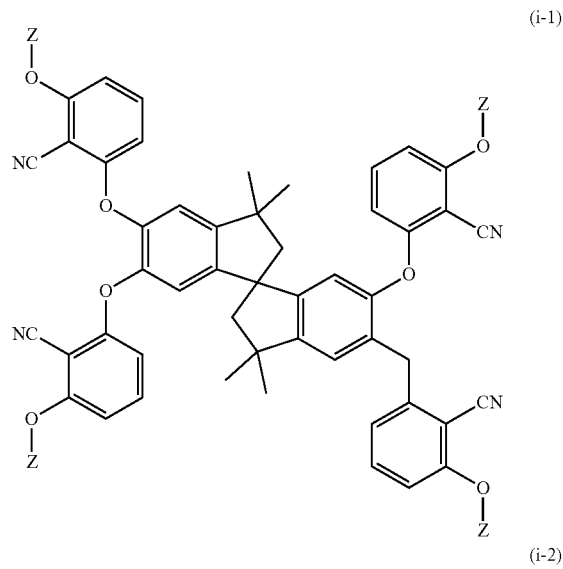

(i-1)

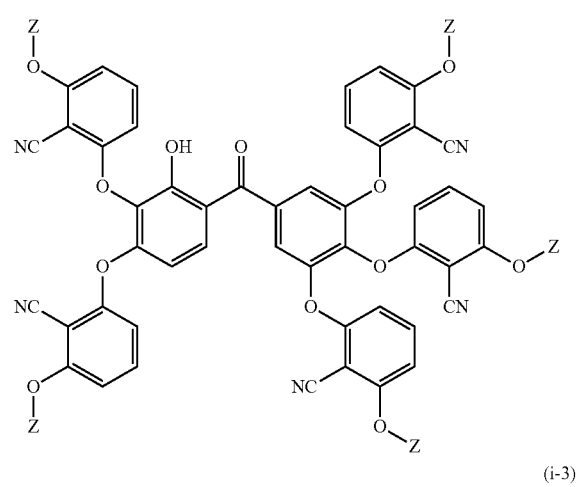

(i-2)

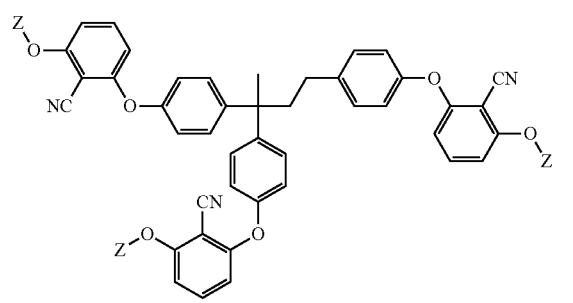

(i-3)

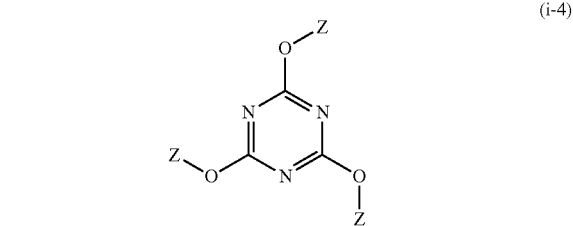

(i-4)

-continued

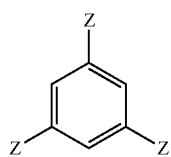
(i-5)

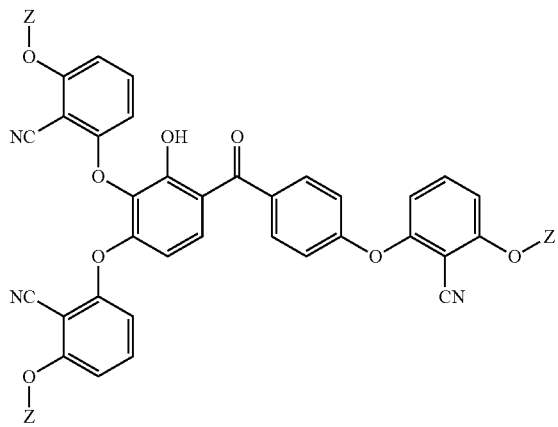
(i-6)

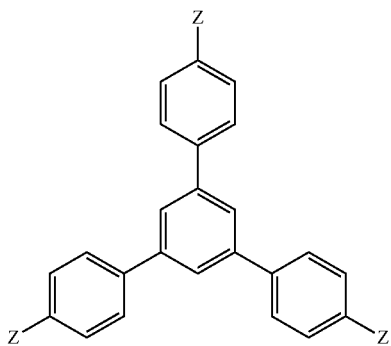
(i-7)

In the above formulae (i-1) to (i-7), Z's each independently represent the group (I).

The compound (i) is preferably any of the compounds (i-1) to (i-7).

The lower limit of a molecular weight of the compound (A) is typically 200, preferably 300, and more preferably 400. The upper limit of the molecular weight is preferably 3,000, more preferably 2,000, and still more preferably 1,500.

Resin (i)

The resin (i) is a resin having the group (I). The resin (i) is exemplified by a resin having an aromatic ring in a main chain thereof, a resin not having an aromatic ring in a main chain thereof but having an aromatic ring in a side chain thereof, and the like. As referred to herein, the "main chain" means a longest chain among chains constituted from atoms in the compound (A). The "side chain" as referred to herein means a chain other than the longest chain, among the chains constituted from the atoms in the compound (A). The resin (i) is typically a compound having two or more groups (I).

When conducting classification according to a type of resin to be the basis, the resin (i) is exemplified by a phenol resin, a naphthol resin, a fluorene resin, an aromatic ring-containing vinyl-based resin, an acenaphthylene resin, an indene resin, an arylene resin, a triazine resin, a pyrene resin, a fullerene resin, a calixarene resin, and the like.

Phenol Resin

The phenol resin is a resin having a structural unit derived from a phenol compound, the structural unit including the group (I). The phenol resin may be synthesized by, for example, allowing the phenol compound to react with an aldehyde compound by using an acidic catalyst or an alkaline catalyst to form the group (I) from a phenol structure of a resulting resin.

Examples of the phenol compound include phenol, cresol, xylenol, resorcinol, bisphenol A, p-tert-butylphenol, p-octylphenol, and the like.

Examples of the aldehyde compound include: aldehydes such as formaldehyde; aldehyde sources such as paraformaldehyde and trioxane; and the like.

Naphthol Resin

The naphthol resin is a resin having a structural unit derived from a naphthol compound, the structural unit including the group (I). The naphthol resin may be synthesized by, for example, allowing the naphthol compound to react with an aldehyde compound by using an acidic catalyst or an alkaline catalyst to form the group (I) from a naphthol structure of a resulting resin.

Examples of the naphthol compound include α-naphthol, β-naphthol, 1,5-dihydroxynaphthalene, 2,7-dihydroxynaphthalene, and the like.

Fluorene Resin

The fluorene resin is a resin having a structural unit derived from a fluorene compound, the structural unit including the group (I). The fluorene resin may be synthesized by, for example, allowing the fluorene compound having a hydroxyaryl structure to react with an aldehyde compound by using an acidic catalyst or an alkaline catalyst to form the group (I) from the hydroxyaryl structure of a resulting resin.

Examples of the fluorene compound include 9,9-bis(4-hydroxyphenyl)fluorene, 9,9-bis(4-hydroxyphenyl)fluorene, 9,9-bis(6-hydroxynaphthyl)fluorene, and the like.

Aromatic Ring-Containing Vinyl-Based Resin

The aromatic ring-containing vinyl-based resin is a resin having a structural unit derived from a compound having an aromatic ring and a polymerizable carbon-carbon double bond, the structural unit including the group (I). The aromatic ring-containing vinyl-based resin may be synthesized by, for example, forming the group (I) from a phenol structure of a resin having a structural unit derived from a compound having: an aromatic ring including a phenolic hydroxyl group; and a polymerizable carbon-carbon double bond.

Acenaphthylene Resin

The acenaphthylene resin is a resin having a structural unit derived from an acenaphthylene compound, the structural unit including the group (I). The acenaphthylene resin may be synthesized by, for example, forming the group (I) from a phenol structure of a resin having a structural unit derived from an acenaphthylene compound having a hydroxyaryl structure.

Indene Resin

The indene resin is a resin having a structural unit derived from an indene compound, the structural unit including the group (I). The indene resin may be synthesized by, for example, forming the group (I) from a hydroxyaryl structure of a resin having a structural unit derived from an indene compound having a hydroxyaryl structure.

Arylene Resin

The arylene resin is a resin having an arylene skeleton including the group (I). The arylene resin may be synthesized by, for example, forming the group (I) from a phenol structure of a resin having an arylene skeleton having a hydroxyaryl structure. Examples of the arylene skeleton include a phenylene skeleton, a naphthylene skeleton, a biphenylene skeleton, and the like.

Triazine Resin

The triazine resin is a resin having a triazine skeleton including the group (I). The triazine resin may be synthesized by, for example, forming the group (I) from a phenol structure of a resin having a triazine skeleton having a hydroxyaryl structure.

Pyrene Resin

The pyrene resin is a resin having a pyrene skeleton including the group (I). The pyrene resin may be synthesized by, for example, forming the group (I) from a phenol structure of a resin having a pyrene skeleton having a hydroxyaryl structure. The resin having a pyrene skeleton having a hydroxyaryl structure is obtained by, for example, allowing a pyrene compound including a phenolic hydroxyl group to react with an aldehyde compound by using an acidic catalyst.

Fullerene Resin

The fullerene resin is a resin having a fullerene skeleton including the group (I). The fullerene resin may be synthesized by, for example, forming the group (I) from a phenol structure of a resin having a fullerene skeleton having a hydroxyaryl structure.

In the case in which the compound (A) is the phenol resin, the naphthol resin, the fluorene resin, the aromatic ring-containing vinyl-based resin, the acenaphthylene resin, the indene resin, the arylene resin, the triazine resin, the pyrene resin or the fullerene resin, the lower limit of a weight average molecular weight (Mw) of the compound (A) is preferably 500 and more preferably 1,000. Meanwhile, the upper limit of the Mw is preferably 50,000, more preferably 10,000, and still more preferably 8,000.

The lower limit of a ratio (Mw/Mn) of the Mw to a number average molecular weight (Mn) of the compound (A) is typically 1, and preferably 1.1. The upper limit of Mw/Mn is preferably 5, more preferably 3, and still more preferably 1.5.

The Mw and the Mn of the compound (A) are determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

Calixarene Resin

The calixarene resin is a cyclic oligomer including the group (I) in which a plurality of aromatic rings, each having a phenolic hydroxyl group bonded thereto, circularly bond to each other via hydrocarbon groups.

Examples of the calixarene resin include resin (hereinafter, may be also referred to as "calixarene resin (i)") having a structure represented by the following formula (1-7), and the like.

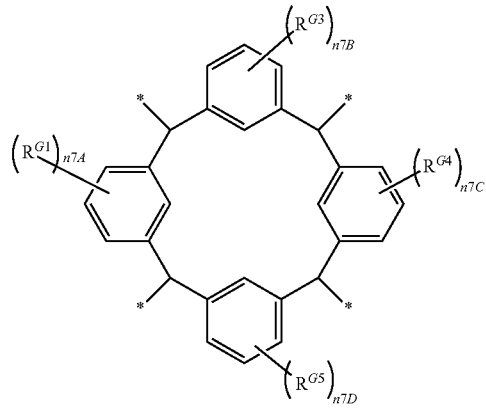

(1-7)

In the above formula (1-7), $R^{G1}$ represents a hydroxy group or $-OR^{G2}$, wherein $R^{G2}$ represents a monovalent organic group having 1 to 20 carbon atoms; $R^{G3}$, $R^{G4}$ and $R^{G5}$ each represent a hydroxy group, a halogen atom, a nitro group or a monovalent organic group having 1 to 20 carbon atoms; and n7A, n7B, n7C and n7D are each an integer of 0 to 3, wherein in a case in which n7A is no less than 2, a plurality of $R^{G1}$s are identical or different from each other, in a case in which there exist a plurality of $R^{G2}$s, the plurality of $R^{G2}$s are identical or different from each other, in a case in which n7B is no less than 2, a plurality of $R^{G3}$s are identical or different from each other, in a case in which n7C is no less than 2, a plurality of $R^{G4}$s are identical or different from each other, and in a case in which n7D is no less than 2, a plurality of $R^{G5}$s are identical or different from each other. It is preferred that n7A, n7B, n7C and n7D are each 0, 1 or 2. In the above formula (1-7), * denotes a site that bonds to the carbon atom on the aromatic ring in $Ar^1$ in the above formula (2).

Examples of the monovalent organic group having 1 to 20 carbon atoms which may be represented by $R^{G2}$ to $R^{G5}$ include groups similar to those exemplified as the monovalent organic group in connection with $R^5$, and the like.

Examples of the resin having a structure represented by the above formula (1-7) include resins represented by the following formulae (i-8) and (i-9), and the like.

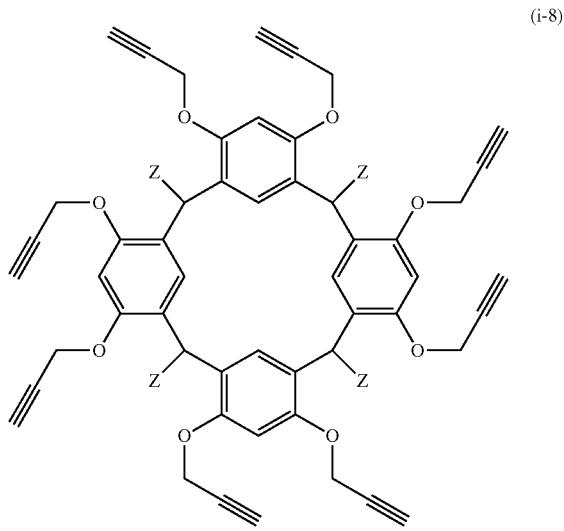

(i-8)

(i-9)

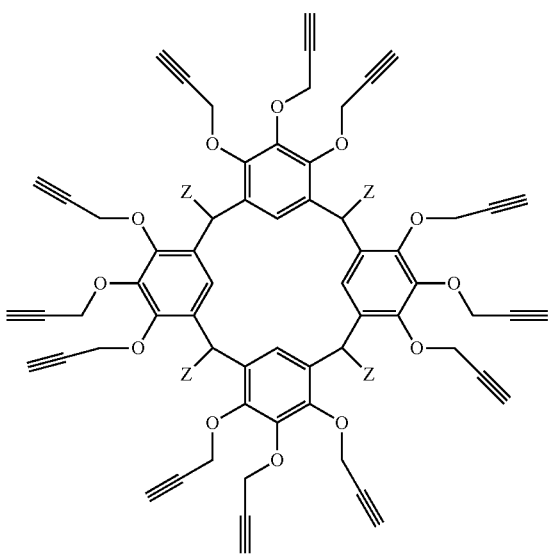

In the above formulae (i-8) and (i-9), Zs each independently represent the group (I).

In the case in which the compound (A) is the calixarene resin, the lower limit of a molecular weight of the calixarene resin is preferably 500, more preferably 700, and still more preferably 1,000 in light of more improvement of the flatness which may be provided by the composition. The upper limit of the molecular weight is preferably 5,000, more preferably 3,000, still more preferably 2,000, and particularly preferably 1,500.

Synthesis Method of Compound (A)

The compound (A) may be synthesized by, for example, using each precursor compound having the group (I) to execute a reaction shown in the following (a) to (d), or the like.

(a) The compound (i) is obtained by using: a phenol compound having the group (I), such as sesamol; a dihaloaromatic compound such as 2,6-difluorobenzonitrile; and a polyvalent phenol compound such as 5,5',6,6'-tetrahydroxy-3,3,3',3'-tetramethyl-1,1-spirobisindane to carry out a dehalogenating hydrogen condensation reaction in the presence of a base such as potassium carbonate, in a solvent such as N,N-dimethylacetamide.

(b) The compound (i) having a benzene skeleton is obtained by using an acetophenone compound having the group (I), such as 3,4-(methylenedioxy)acetophenone to carry out a trimerizing reaction in the presence of an acid such as dodecylbenzenesulfonic acid in a solvent such as m-xylene.

(c) The resin (i) is obtained by using a compound that includes a carbon-carbon double bond-containing group and has the group (I), such as 5-vinyl-1,3-benzodioxole to carry out a polymerization reaction in the presence of a polymerization initiator such as 2,2-azobisisobutyrate in a solvent such as methyl ethyl ketone.

(d) A calixarene resin (i) is obtained by using: an aromatic aldehyde compound having the group (I). such as piperonal; and a phenol compound such as resorcinol to carry out a condensation reaction in the presence of an acid such as hydrochloric acid in a solvent such as ethanol.

The compound (A) to which other group(s) has/have been introduced can be obtained by carrying out a dehalogenating hydrogen condensation reaction of the phenolic hydroxyl group included in the compound synthesized as described above, using, for example, an organic halide such as propargylbromide in the presence of a base such as tetramethylammonium hydroxide in a solvent such as 4-methyl-2-pentanone or methanol.

The compound (A) other than those in (a) to (d) described above can also be synthesized by a known method similar to those described above.

The upper limit of a percentage content of carbon atoms in the compound (A) is preferably 95% by mass, more preferably 90% by mass, and still more preferably 85% by mass. The upper limit of the percentage content of carbon atoms is preferably 40% by mass, more preferably 45% by mass, still more preferably 50% by mass, and particularly preferably 55% by mass. When the percentage content of carbon atoms in the compound (A) falls within the above range, the solvent resistance can be improved.

The upper limit of a percentage content of hydrogen atoms in the compound (A) is preferably 6.5% by mass, more preferably 6.0% by mass, still more preferably 5.0% by mass, and particularly preferably 4.0% by mass. The lower limit of the percentage content of hydrogen atom is, for example, 0.1% by mass. When the percentage content of hydrogen atoms in the compound (A) falls within the above range, the flexural resistance of a resist underlayer film pattern in etching of the substrate can be further improved.

The lower limit of a percentage content of the compound (A) in the solid content of the composition is preferably 50% by mass, more preferably 70% by mass, and still more preferably 85% by mass. The upper limit of the percentage content is, for example, 100% by mass. The "solid content" as referred to herein means components other than the solvent (B) in the composition.

The lower limit of the percentage content of the compound (A) in the composition is preferably 1% by mass, more preferably 3% by mass, and still more preferably 5% by mass. The upper limit of the percentage content is preferably 50% by mass, more preferably 30% by mass, and still more preferably 15% by mass.

(B) Solvent

The solvent (B) is not particularly limited as long as it can dissolve or disperse the compound (A), and the optional component(s) which may be contained as needed.

The solvent (B) is exemplified by an alcohol solvent, a ketone solvent, an ether solvent, an ester solvent, a nitrogen-containing solvent, and the like. The solvent (B) may be used either alone of one type, or in combination of two or more types thereof.

Examples of the alcohol solvent include: monohydric alcohol solvents such as methanol, ethanol and n-propanol; polyhydric alcohol solvents such as ethylene glycol and 1,2-propylene glycol; and the like.

Examples of the ketone solvent include: chain ketone solvents such as methyl ethyl ketone and methyl-iso-butylketone; cyclic ketone solvents such as cyclohexanone; and the like.

Examples of the ether solvent include: polyhydric alcohol ether solvents, e.g., chain ether solvents such as n-butyl ether, and cyclic ether solvents such as tetrahydrofuran; polyhydric alcohol partial ether solvents such as diethylene glycol monomethyl ether; and the like.

Examples of the ester solvent include: carbonate solvents such as diethyl carbonate; mono ester acetate solvents such as methyl acetate and ethyl acetate; lactone solvents such as γ-butyrolactone; polyhydric alcohol partial ether carboxylate solvents such as diethylene glycol monomethyl ether acetate and propylene glycol monomethyl ether acetate; ester lactate solvents such as methyl lactate and ethyl lactate; and the like.

Examples of the nitrogen-containing solvent include: chain nitrogen-containing solvents such as N,N-dimethylacetamide; cyclic nitrogen-containing solvents such as N-methylpyrrolidone; and the like.

Of these, the ether solvent and/or the ester solvent are/is preferred, and an ether solvent and/or an ester solvent each having a glycol structure are/is more preferred in light of superior film formability.

Examples of the ether solvent and the ester solvent each having a glycol structure include propylene glycol monomethyl ether, propylene glycol monoethyl ether, propylene glycol monopropyl ether, propylene glycol monomethyl ether acetate, propylene glycol monoethyl ether acetate, propylene glycol monopropyl ether acetate, and the like. Of these, propylene glycol monomethyl ether acetate is particularly preferred.

The lower limit of a percentage content of the ether solvent and the ester solvent, each having a glycol structure, in the solvent (B) is preferably 20% by mass, more preferably 60% by mass, still more preferably 90% by mass, and particularly preferably 100% by mass.

Optional Components

The composition may contain as optional component(s), an acid generating agent, a crosslinking agent, a surfactant, an adhesion aid, and/or the like.

Acid Generating Agent

The acid generating agent generates an acid by an action of heat and/or light to promote the crosslinking of molecules of the compound (A). When the composition contains the acid generating agent, a crosslinking reaction of molecules of the compound (A) is promoted and consequently the hardness of the film to be formed can be further increased. The acid generating agent may be used either alone of one type, or in combination of two or more types thereof.

The acid generating agent is exemplified by an onium salt compound, an N-sulfonyloxyimide compound, and the like.

Crosslinking Agent

The crosslinking agent forms crosslinking bonds between components such as the compound (A) in the composition, or forms cross-linked structures by molecules of itself, through an action of heat and/or an acid. When the composition contains the crosslinking agent, an increase in hardness of the film to be formed is enabled. The crosslinking agent may be used either alone of one type, or in combination of two or more types thereof.

The crosslinking agent is exemplified by a polyfunctional (meth)acrylate compound, an epoxy compound, a hydroxymethyl group-substituted phenol compound, an alkoxyalkyl group-containing phenol compound, a compound having an alkoxyalkylated amino group, and the like.

Preparation Procedure of Composition

The composition may be prepared, for example, by mixing the compound (A), the solvent (B), and as needed, the optional component(s) in a certain ratio, preferably followed by filtering a thus resulting mixture through a membrane filter, etc. having a pore size of no greater than 0.1 µm. The lower limit of a solid content concentration of the composition is preferably 0.1% by mass, more preferably 1% by mass, still more preferably 3% by mass, and particularly preferably 5% by mass. The upper limit of the solid content concentration is preferably 50% by mass, more preferably 30% by mass, still more preferably 20% by mass, and particularly preferably 15% by mass.

The composition of the embodiment of the invention enables formation of a film that is superior in flatness, wet peel resistance, and flexural resistance of a pattern, with solvent resistance being maintained, and can therefore be suitably used for formation of a resist underlayer film in production of a semiconductor device and the like.

Film

The film of the embodiment of the invention is formed from the composition of the embodiment of the present invention. Since the film is formed from the composition described above, the film is superior in flatness, wet peel resistance and flexural resistance of the pattern, with solvent resistance being maintained.

Film-Forming Method

The film-forming method of the embodiment of the invention is exemplified by a film-forming method (I), a film-forming method (II), and the like.

Film-Forming Method (I)

The film-forming method (I) includes the applying step (I) and the heating step (I). The film-forming method (I) enables formation of a film that is superior in flatness, wet peel resistance, and flexural resistance of a pattern, with solvent resistance being maintained since the composition of the embodiment of the present invention is used. Hereinafter, each step will be described.

Applying Step (I)

In this step, the composition of the embodiment of the invention is applied directly or indirectly on at least an upper face side of a substrate to form a coating film.

Examples of the substrate include a silicon wafer, a wafer coated with aluminum, and the like. The applying procedure of the composition is not particularly limited, and for example, an appropriate procedure such as spin coating, cast coating and roll coating may be employed to form the coating film.

Heating Step (I)

In this step, the coating film obtained by the applying step (I) is heated to form a film.

Heating of the coating film is typically carried out in an ambient air, but may be carried out in a nitrogen atmosphere. A heating temperature is, for example, no less than 200° C. and no greater than 600° C. A heating time period is, for example, no less than 15 sec and no greater than 1,200 sec.

The coating film may be preheated at a temperature of no less than 60° C. and no greater than 150° C. before being heated at a temperature of no less than 200° C. and no greater than 600° C. The lower limit of the heating time period in the preheating is preferably 10 sec, and more preferably 30 sec. The upper limit of the heating time period is preferably 300 sec, and more preferably 180 sec.

It is to be noted that in the film-forming method (I), the film is formed through the heating of the coating film; however, in a case in which the composition contains the acid generating agent and the acid generating agent is a radiation-sensitive acid generating agent, it is also possible to form the resist underlayer film by hardening the film through a combination of an exposure and heating. The radioactive ray used for the exposure may be appropriately selected from: electromagnetic waves such as visible rays, ultraviolet rays, far ultraviolet rays, X-rays and γ-rays; particle rays such as electron beams, molecular beams and ion beams; and the like in accordance with the type of the acid generating agent.

The lower limit of the average thickness of the film to be formed is preferably 30 nm, more preferably 50 nm, and still more preferably 100 nm. The upper limit of the average thickness is preferably 3,000 nm, more preferably 2,000 nm, and still more preferably 500 nm.

Film-Forming Method (II)

The film-forming method (II) includes the applying step (II) and the heating step (II). The film-forming method (II) enables formation of a film that is superior in flatness, wet peel resistance, and flexural resistance of a pattern, with solvent resistance being maintained since the composition of the embodiment of the present invention is used. Hereinafter, each step will be described.

Applying Step (II)

In this step, the composition of the embodiment of the invention is applied directly or indirectly on at least an upper face side of a substrate to form a coating film. This step is similar to the applying step (I) described above.

Heating Step (II)

In this step, the coating film obtained by the applying step (II) is heated to form a film.

Heating of the coating film is typically carried out in an ambient air, but may be carried out in a nitrogen atmosphere. The lower limit of a heating temperature is typically 300° C., preferably 320° C., and more preferably 340° C. The upper limit of the heating temperature is preferably 500° C., more preferably 450° C., and still more preferably 400° C. When the heating temperature is no less than 300° C., hardening in a state with high fluidity is enabled, thereby leading to a further improvement of the flatness. The lower limit of the heating time period is preferably 15 sec, more preferably 30 sec, and still more preferably 45 sec. The upper limit of the heating time period is preferably 1,200 sec, more preferably 600 sec, and still more preferably 300 sec.

The coating film may be preheated at a temperature of no less than 100° C. and no greater than 200° C. before being heated at a temperature of no less than 300° C. and no greater than 500° C. The lower limit of the heating time period in the preheating is preferably 10 sec, and more preferably 30 sec. The upper limit of the heating time period is preferably 300 sec, and more preferably 180 sec.

It is to be noted that in the film-forming method (II), the film is formed through the heating of the coating film; however, in a case in which the composition contains the acid generating agent and the acid generating agent is a radiation-sensitive acid generating agent, it is also possible to form the resist underlayer film by hardening the film through a combination of an exposure and heating. The radioactive ray used for the exposure may be appropriately selected from: electromagnetic waves such as visible rays, ultraviolet rays, far ultraviolet rays, X-rays and γ-rays; particle rays such as electron beams, molecular beams and ion beams; and the like in accordance with the type of the acid generating agent.

The lower limit of the average thickness of the film formed is preferably 30 nm, more preferably 50 nm, and still more preferably 100 nm. The upper limit of the average thickness is preferably 3,000 nm, more preferably 2,000 nm, and still more preferably 500 nm.

Patterned Substrate-Producing Method

The patterned substrate-producing method of the embodiment of the invention is exemplified by a patterned substrate-producing method (I), a patterned substrate-producing method (II), and the like.

Patterned Substrate-Producing Method (I)

The patterned substrate-producing method (I) includes the applying step (III), the heating step (III), the silicon-containing film-forming step (I), and the silicon-containing film-removing step.

According to the patterned substrate-producing method (I), use of the film, which was obtained by the film-forming method described above, being superior in flatness, wet peel resistance, and flexural resistance of the pattern, with the solvent resistance maintained enables a patterned substrate having a superior pattern configuration to be obtained.

In the patterned substrate-producing method (I), the silicon-containing film-forming step (I) may be carried out again after the silicon-containing film-removing step, as needed. Also, after the silicon-containing film-forming step (I), a step of forming a resist pattern on an upper face side of the silicon-containing film (hereinafter, may be also referred to as "resist pattern-forming step (I)"); and a step of etching the substrate using the resist pattern as a mask (hereinafter, may be also referred to as "etching step (I)") may be further included. Hereinafter, each step will be described.

Applying Step (III)

In this step, the composition of the embodiment of the invention is applied directly or indirectly on at least an upper face side of a substrate to form a coating film. This step is similar to the applying step (I) described above.

Heating Step (III)

In this step, the coating film obtained by the applying step (III) is heated to form a film. This step is similar to the heating step (I) described above.

Silicon-Containing Film-Forming Step (I)

In this step, a silicon-containing film is formed on an upper face side of the film obtained by the heating step (III).

The silicon-containing film is formed by, for example: applying a composition for silicon-containing film formation on an upper face side of the film to form a coating film; and hardening the coating film typically by subjecting the coating film to an exposure and/or heating. As a commercially available product of the composition for silicon-containing film formation, "NFC SOG01", "NFC SOG04", and "NFC SOG080" (all available from JSR Corporation) or the like may be used.

Examples of the radioactive ray for use in the exposure include: electromagnetic waves such as visible rays, ultraviolet rays, far ultraviolet rays, X-rays and γ-rays; particle rays such as electron beams, molecular beams and ion beams; and the like in accordance with the type of the acid generating agent.

The lower limit of a temperature in heating the coating film is preferably 90° C., more preferably 150° C., and still more preferably 200° C. The upper limit of the temperature is preferably 550° C., more preferably 450° C., and still more preferably 300° C. The lower limit of an average thickness of the silicon-containing film to be formed is preferably 1 nm, more preferably 10 nm, and still more preferably 20 nm. The upper limit of the average thickness is preferably 20,000 nm, more preferably 1,000 nm, and still more preferably 100 nm.

Silicon-Containing Film-Removing Step

In this step, the silicon-containing film obtained by the silicon-containing film-forming step (I) is removed with a basic liquid. According to this step, the silicon-containing film is removed without greatly causing damage to the substrate or the film, and reprocessing of a film-attached substrate having been provided with the film thereon is enabled. This step may be carried out also on a silicon-containing film unpatterned or patterned before the etching step (I) described later. More specifically, for example, in a case in which defects are generated in the silicon-containing film-forming step (I), and/or in a case in which defects are generated on the patterned silicon-containing film before the etching step (I) described later, carrying out this silicon-containing film-removing step enables the process to be restarted from the silicon-containing film-forming step (I), without discarding the film-attached substrate.

A procedure for removing the silicon-containing film is not particularly limited as long as the procedure enables the basic liquid tobe brought into contact with the silicon-containing film for a certain period of time. For example, exemplified procedures may include subjecting the film-attached substrate having been provided with the silicon-containing film thereon to: immersion in the basic liquid; spraying of the basic liquid; an applying of the basic liquid; and the like.

The basic liquid is exemplified by alkaline hydrogen peroxide water and the like. More specifically, an aqueous solution mixture of ammonia and hydrogen peroxide (25% by mass aqueous ammonia solution/30% by mass aqueous hydrogen peroxide solution/water=1/2/40 (mass ratio); aqueous solution mixture (SC1)) is particularly preferred. A procedure for removing the silicon-containing film in the case of using the alkaline hydrogen peroxide water is not particularly limited as long as the procedure enables alkaline hydrogen peroxide water to be brought into contact with the silicon-containing film under a heating condition for a certain period of time. For example, exemplified procedures may include subjecting the substrate having the silicon-containing film to: immersion in heated alkaline hydrogen peroxide water; spraying of alkaline hydrogen peroxide water in a heat environment; an applying of heated alkaline hydrogen peroxide water; and the like. After each of these procedures, the film-attached substrate is preferably washed with water and dried.

In the case in which alkaline hydrogen peroxide water is used, the lower limit of a temperature is preferably 40° C., and more preferably 50° C. The upper limit of the temperature is preferably 90° C., and more preferably 80° C.

The lower limit of a time period of the immersion in the procedure including immersion is preferably 1 min, more preferably 2 min, and still more preferably 3 min. The upper limit of the time period is preferably 30 min, and more preferably 15 min.

Resist Pattern-Forming Step (I)

In this step, a resist pattern is formed on an upper face side of the film described above. This step may be carried out by, for example, using a resist composition, or the like.

When the resist composition is used, specifically, the resist film is formed by applying the resist composition such that a resultant resist film has a predetermined thickness and thereafter subjecting the resist composition to prebaking to evaporate away the solvent in the coating film.

Examples of the resist composition include a chemically amplified positive or negative resist composition that contains a radiation-sensitive acid generating agent; a positive resist composition containing an alkali-soluble resin and a quinone diazide-based photosensitizing agent; a negative resist composition containing an alkali-soluble resin and a crosslinking agent; and the like.

The lower limit of a solid content concentration of the resist composition is preferably 0.3% by mass, and more preferably 1% by mass. The upper limit of the solid content concentration of the resist composition is preferably 50% by mass, and more preferably 30% by mass. Moreover, the resist composition is generally used for forming a resist film, for example, after being filtered through a filter with a pore size of no greater than 0.2 µm. It is to be noted that a commercially available resist composition may be used as is in this step.

The applying procedure of the resist composition is not particularly limited, and examples thereof include a spin-coating procedure, and the like. The temperature of the prebaking may be appropriately adjusted in accordance with the type of the resist composition employed and the like; however, the lower limit of the temperature is preferably 30° C., and more preferably 50° C. The upper limit of the aforementioned temperature is preferably 200° C., and more preferably 150° C. The lower limit of a time period for the prebaking is preferably 10 sec, and more preferably 30 sec. The upper limit of the time period for the prebaking is preferably 600 sec, and more preferably 300 sec.

Next, the resist film formed is exposed by selective irradiation with a radioactive ray. The radioactive ray used in the exposure may be appropriately selected from: electromagnetic waves such as visible rays, ultraviolet rays, far ultraviolet rays, X-rays and γ-rays; and particle rays such as electron beams, molecular beams and ion beams in accordance with the type of the radiation-sensitive acid generating agent to be used in the resist composition. Among these, far ultraviolet rays are preferred, a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) or an extreme ultraviolet ray (EUV; wavelength: 13.5 nm, etc.) is more preferred, and a KrF excimer laser beam, an ArF excimer laser beam or EUV is still more preferred.

Post-baking may be carried out after the exposure for the purpose of improving resolution, pattern profile, developability, and the like. The temperature of the post-baking may be appropriately adjusted in accordance with the type of the resist composition to be employed and the like; however, the lower limit of the temperature is preferably 50° C., and more preferably 70° C. The upper limit of the aforementioned temperature is preferably 200° C., and more preferably 150° C. The lower limit of a time period for the post-baking is preferably 10 sec, and more preferably 30 sec. The upper limit of the time period for the post-baking is preferably 600 sec, and more preferably 300 sec.

Next, the resist film exposed is developed with a developer solution to form a resist pattern. The development may be either a development with an alkali or a development with an organic solvent. In the case of the development with an alkali, examples of the developer solution include a basic aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water-soluble organic solvent, e.g., an alcohol such as methanol or ethanol, a surfactant, or the like may be added to the basic aqueous solution. Alternatively, in the case of the development with an organic solvent, examples of the developer solution include a variety of organic solvents exemplified as the solvent (B) in relation to the composition described above, and the like.

A predetermined resist pattern is formed by the development with the developer solution, followed by washing and drying.

In carrying out the resist pattern-forming step, outside of using the resist composition described above, another process may be employed; for example, a nanoimprinting may be adopted, or a directed self-assembling composition may be also used.

Etching Step (I)

In this step, the substrate is etched using the aforementioned resist pattern as a mask to form a pattern on the substrate. The etching may be conducted once or multiple times. In other words, the etching may be conducted sequentially with patterns obtained by the etching as masks. However, in light of obtaining a pattern with a more favorable configuration, the etching is preferably conducted multiple times. In the case in which the etching is conducted multiple times, the silicon-containing film, the film, and the substrate are subjected to the etching sequentially in this order. The etching step may be exemplified by dry etching, wet etching, and the like. Of these, in light of achieving a pattern with a more favorable configuration, dry etching is preferred. For example, gas plasma such as oxygen plasma or the like may be used in the dry etching. After the dry etching, the substrate having a predetermined pattern can be obtained.

Patterned Substrate-Producing Method (II)

The patterned substrate-producing method (II) includes the applying step (IV), the heating step (IV), the silicon-containing film-forming step (II), the resist pattern-forming step (II), and the etching step (II).

According to the patterned substrate-producing method (II), use of the film, which was obtained by the film-forming method described above, being superior in flatness, wet peel resistance, and flexural resistance of the pattern, with the solvent resistance maintained enables a patterned substrate having a superior pattern configuration to be obtained. Each step will be described below.

Applying Step (IV)

In this step, the composition of the embodiment of the invention is applied directly or indirectly on at least an upper face side of a substrate to form a coating film. This step is similar to the applying step (I) described above.

Heating Step (IV)

In this step, the coating film obtained by the applying step (IV) is heated to form a film. This step is similar to the heating step (I) described above.

Resist Pattern-Forming Step (II) In this step, a resist pattern is formed on an upper face side of the film described above. This step is similar to the resist pattern-forming method (I) described above.

Etching Step (II)

In this step, etching is conducted with the aforementioned resist pattern as a mask to form a pattern on the substrate. This step is similar to the etching step (I) described above.

EXAMPLES

Hereinafter, the embodiment of the present invention will be explained in more detail by way of Examples, but the present invention is not in any way limited to these Examples. Measuring methods for various types of physical properties are shown below.

Weight Average Molecular Weight (Mw)

In the case in which the compound (A) is a polymer, the Mw of the compound (A) was determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

The percentage content of carbon atoms and the percentage content of hydrogen atoms in the compound (A) was determined by calculation.

Average Thickness of Film

The average thickness of the film was determined using a spectroscopic ellipsometer ("M2000D" available from J. A. WOOLLAM Co.).

Synthesis of Compound (A)

Compounds (hereinafter, may be also referred to as "compounds (A-1) to (A-9)") represented by the following formulae (A-1) to (A-9), and resins (hereinafter, may be also referred to as "resins (A-10) to (A-11)") represented by the following formulae (A-10) to (A-11) were synthesized in accordance with the following procedure.

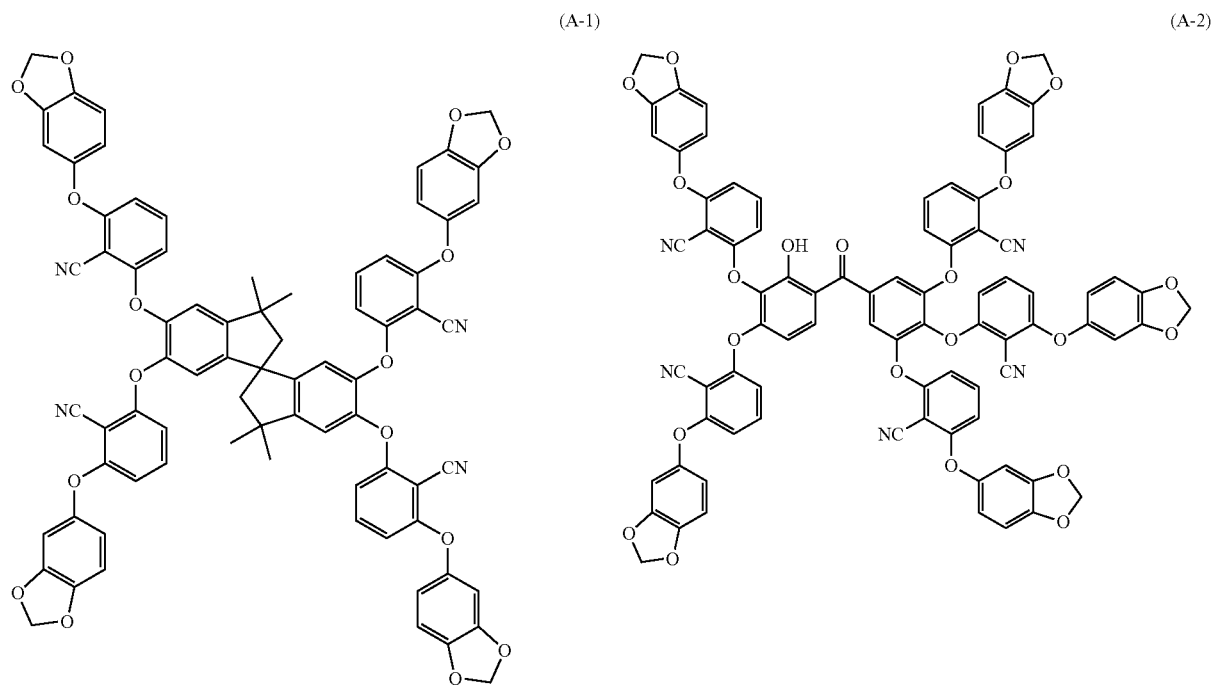

-continued
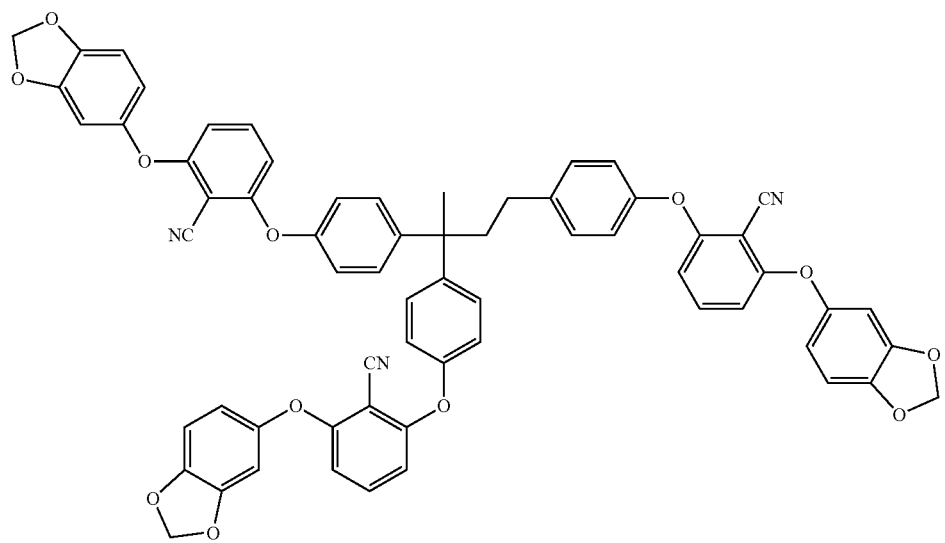
(A-3)
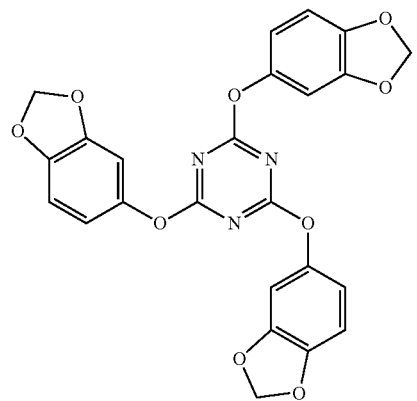
(A-4)
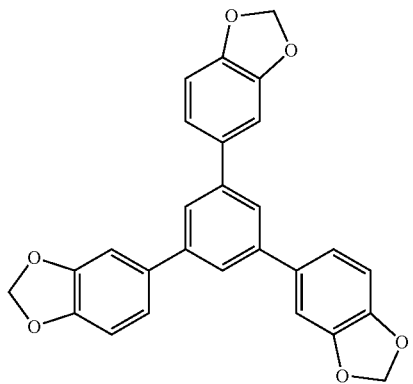
(A-5)
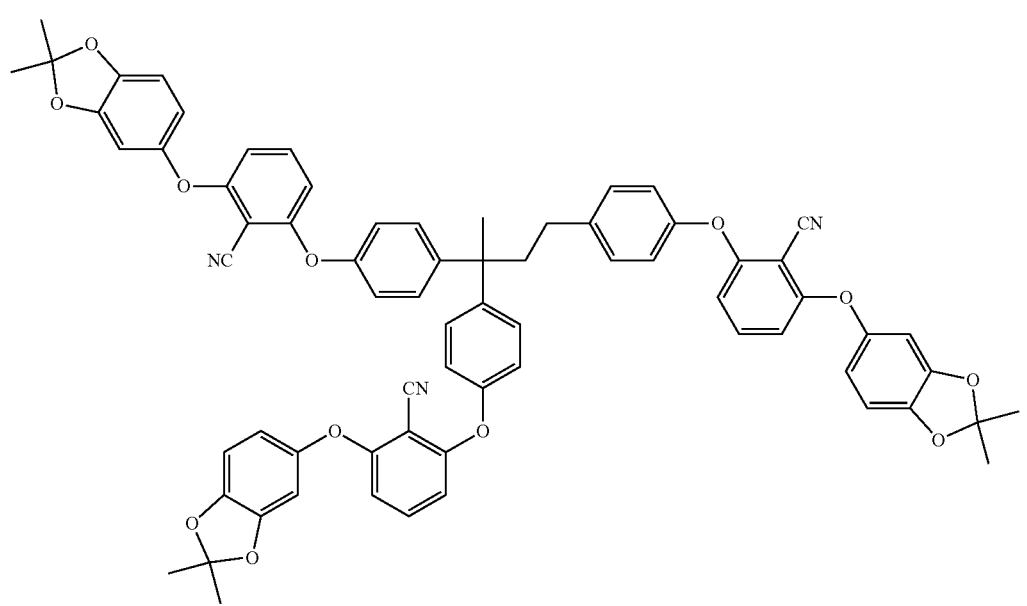
(A-6)

(A-7)
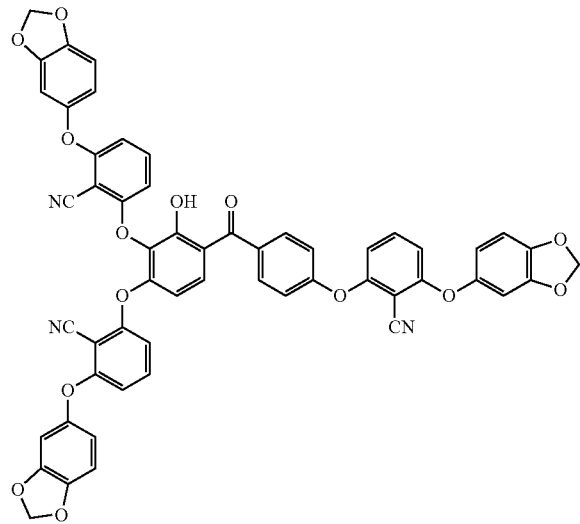
(A-8)
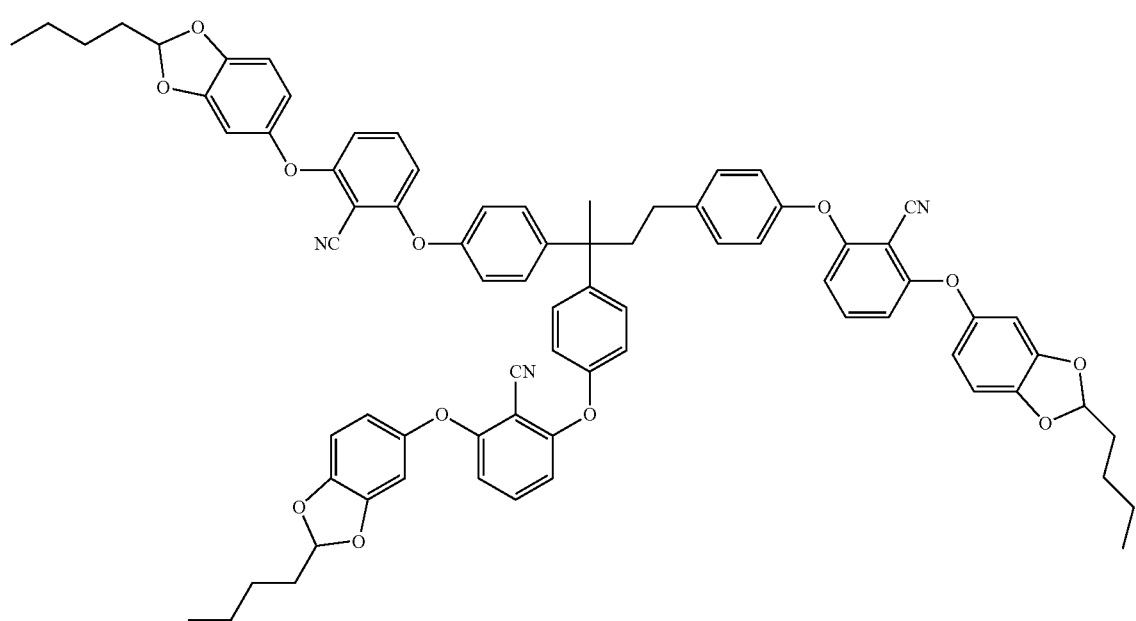

(A-9)

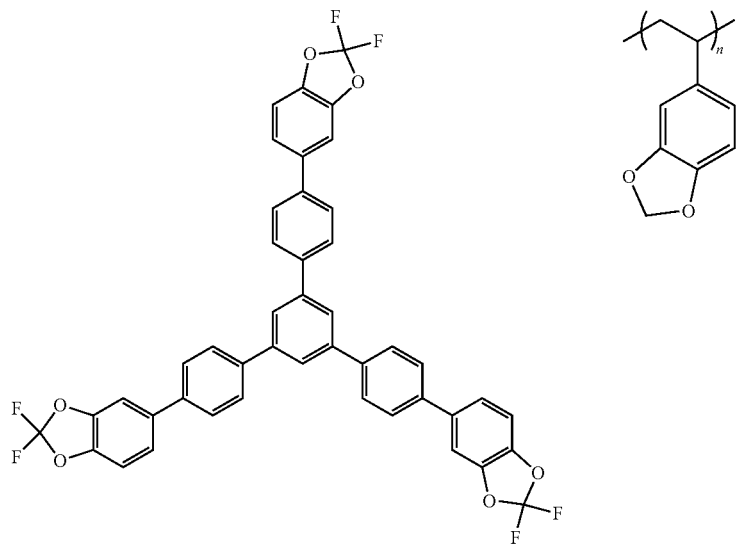

(A-10)

(A-11)

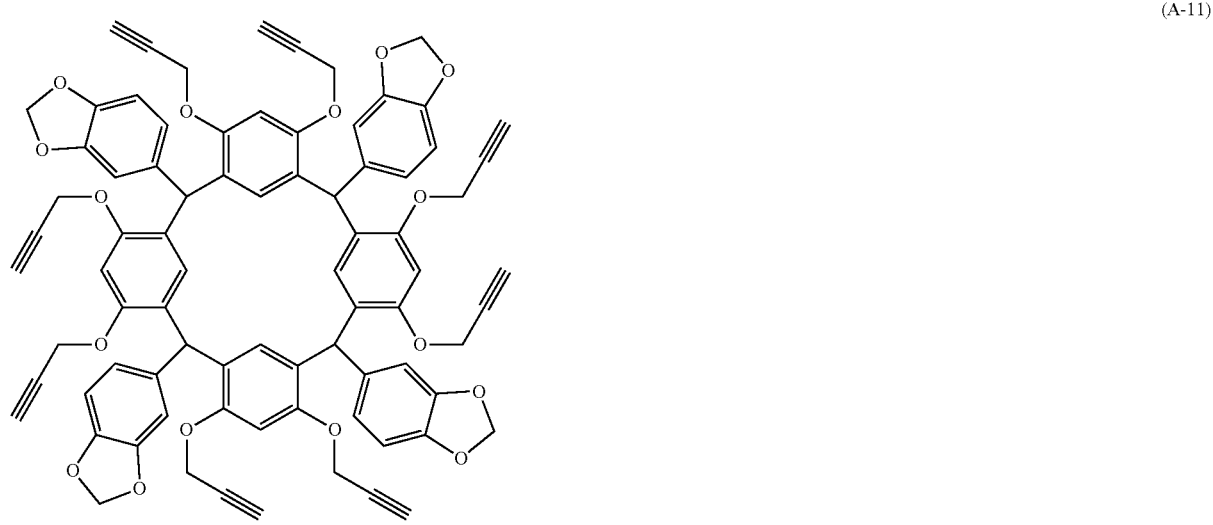

Synthesis Example 1-1

Into a reaction vessel, 30.0 g of sesamol, 28.8 g of 2,6-difluorobenzonitrile, 30.0 g of potassium carbonate, and 146.9 g of N,N-dimethylacetamide were added and a reaction was allowed at 120° C. for 7 hrs in a nitrogen atmosphere. Thereafter the reaction solution was cooled to room temperature and thereto were further added 14.1 g of 5,5', 6,6'-tetrahydroxy-3,3,3',3'-tetramethyl-1,1-spirobisindane, 17.2 g of potassium carbonate, and 14.1 g of N,N-dimethylacetamide. The compound (A-1) was obtained by allowing a reaction at 130° C. for 12 hrs.

Synthesis Example 1-2 to 1-4, and 1-6 to 1-8

The compounds (A-2) to (A-4) and (A-6) to (A-8) were synthesized similarly to Synthesis Example 1-1 through appropriately selecting the precursors.

Synthesis Example 1-5

Into a reaction vessel, 20.0 g of 3,4-(methylenedioxy) acetophenone and 20.0 g of m-xylene were charged and then 4.0 g of dodecylbenzenesulfonic acid was added thereto in a nitrogen atmosphere. The compound (A-5) was obtained by allowing a reaction at 140° C. for 16 hrs.

Synthesis Example 1-9

The compound (A-9) was synthesized similarly to Synthesis Example 1-5 through appropriately selecting the precursor.

Synthesis Example 1-10

Into a reaction vessel, 14.0 g of methyl ethyl ketone was charged and a liquid temperature was elevated to 80° C. in a nitrogen atmosphere. A solution separately prepared from 20.0 g of 5-vinyl-1,3-benzodioxole, 1.6 g of 2,2-azobisisobutyrate, and 26.0 g of methyl ethyl ketone was added dropwise to the aforementioned liquid over 3 hrs while maintaining the temperature at 80° C. Further, after completion of the dropwise addition, the resin (A-10) was obtained by aging the mixture at 80° C. for 3 hrs.

Synthesis Example 1-11

Into a reaction vessel, 15.0 g of resorcinol, 20.5 g of piperonal, and 177.3 g of ethanol were charged and dissolution was allowed at room temperature in a nitrogen atmosphere. To a thus resulting solution was added 40.1 g of concentrated hydrochloric acid dropwise over 1 hour. Thereafter, the solution temperature was elevated to 80° C. and aging was allowed for 7 hrs. After completion of the aging, the solution temperature was lowered to room temperature by cooling. Thereafter, a reddish-brown solid matter thus precipitated was collected by removing an ethanol solution through filtration. Accordingly, a solid matter to serve as a precursor was obtained.

Next, to a reaction vessel, 15.0 g of the precursor obtained as described above, 30.0 g of 4-methyl-2-pentanone, 15.0 g of methanol, and 45.2 g of a 25% by mass aqueous tetramethylammonium hydroxide solution were charged and dissolution was allowed at room temperature in a nitrogen atmosphere. Thereafter, temperature elevation to 50° C. was followed by dropwise addition of 14.7 g of propargylbromide over 30 min. The resin (A-11) was obtained by allowing aging directly thereafter at 50° C. for 6 hrs.

Synthesis Example 2-1

Into a reaction vessel, 250.0 g of m-cresol, 125.0 g of 37% by mass formalin, and 2 g of anhydrous oxalic acid were added and a reaction was allowed at 100° C. for 3 hrs and at 180° C. for 1 hour in a nitrogen atmosphere. Thereafter, a resin represented by the following formula (a-1) was obtained by eliminating an unreacted monomer under a reduced pressure. The Mw of the resin (a-1) thus obtained was 11,000.

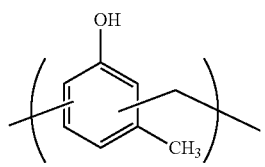

(a-1)

Preparation of Composition

The compound (A), the solvent (B), an acid generating agent (hereinafter, may be also referred to as "(C) acid generating agent"), and a crosslinking agent (hereinafter, may be also referred to as "(D) crosslinking agent") used in preparation of the compositions are as presented below.

(A) Compound
Examples: the compounds (A-1) to (A-9) and the resins (A-10) and (A-11) synthesized as described above
Comparative Examples: the resin (a-1) synthesized as described above
(B) Solvent
B-1: propylene glycol monomethyl ether acetate
(C) Acid Generating Agent
C-1: bis(4-t-butylphenyl)iodonium nonafluoro-n-butane-sulfonate (a compound represented by the following formula (C-1))

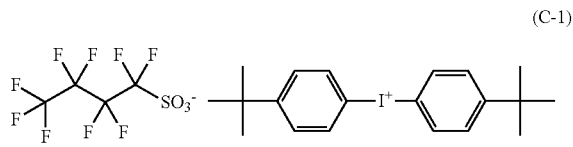

(C-1)

(D) Crosslinking Agent
D-1: 1,3,4,6-tetrakis(methoxymethyl)glycoluril (a compound represented by the following formula (D-1))

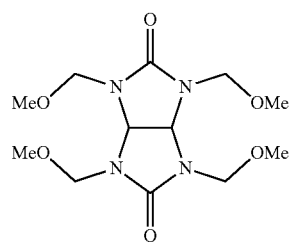

(D-1)

Example 1-1

Ten parts by mass of (A-1) as the compound (A) were dissolved in 90 parts by mass of (B-1) as the solvent (B). A solution thus obtained was filtered through a membrane filter having a pore size of 0.1 μm to prepare a composition (J-1).

Examples 1-2 to 1-11 and Comparative Example 1-1

Compositions (J-2) to (J-11) and (CJ-1) were prepared by a similar operation to that of Example 1-1 except that each type of the component at the content shown in Table 1 was used. In Table 1, "-" indicates that a corresponding component was not used.

TABLE 1

| | Composition | type | (A) Compound percentage content of hydrogen atoms (% by mass) | (A) Compound percentage content of carbon atoms (% by mass) | content (parts by mass) | (B) Solvent type | (B) Solvent content (parts by mass) | (C) Acid generating agent type | (C) Acid generating agent content (parts by mass) | (D) Crosslinking agent type | (D) Crosslinking agent content (parts by mass) |
|---|---|---|---|---|---|---|---|---|---|---|---|
| Example 1-1 | J-1 | A-1 | 4.07 | 71.72 | 10 | B-1 | 90 | — | — | — | — |
| Example 1-2 | J-2 | A-2 | 3.10 | 68.07 | 10 | B-1 | 90 | — | — | — | — |
| Example 1-3 | J-3 | A-3 | 4.14 | 73.48 | 10 | B-1 | 90 | — | — | — | — |
| Example 1-4 | J-4 | A-4 | 3.09 | 58.89 | 10 | B-1 | 90 | — | — | — | — |
| Example 1-5 | J-5 | A-5 | 4.14 | 73.96 | 10 | B-1 | 90 | — | — | — | — |
| Example 1-6 | J-6 | A-6 | 4.91 | 74.38 | 10 | B-1 | 90 | — | — | — | — |
| Example 1-7 | J-7 | A-7 | 3.26 | 68.96 | 10 | B-1 | 90 | — | — | — | — |
| Example 1-8 | J-8 | A-8 | 5.56 | 75.16 | 10 | B-1 | 90 | — | — | — | — |

TABLE 1-continued

|  | Compo-sition | (A) Compound | | | (B) Solvent | | (C) Acid generating agent | | (D) Crosslinking agent | |
|---|---|---|---|---|---|---|---|---|---|---|
|  |  | type | percentage content of hydrogen atoms (% by mass) | percentage content of carbon atoms (% by mass) | content (parts by mass) | type | content (parts by mass) | type | content (parts by mass) | type | content (parts by mass) |
| Example 1-9 | J-9 | A-9 | 3.13 | 69.76 | 10 | B-1 | 90 | — | — | — | — |
| Example 1-10 | J-10 | A-10 | 5.44 | 72.95 | 10 | B-1 | 90 | — | — | — | — |
| Example 1-11 | J-11 | A-11 | 4.43 | 75.45 | 10 | B-1 | 90 | — | — | — | — |
| Comparative Example 1-1 | CJ-1 | a-1 | 6.71 | 79.96 | 10 | B-1 | 90 | C-1 | 0.5 | D-1 | 3 |

Film Formation

Examples 2-1 to 2-11 and Comparative Example 2-1

The composition prepared as described above was applied on a silicon wafer (substrate) with a spin coater ("CLEAN TRACK ACT12" available from Tokyo Electron Limited) by way of a spin-coating procedure. Next, heating (baking) in an ambient air atmosphere at the heating temperature (° C.) for the heating time period (sec) shown in Table 2 below was followed by cooling at 23° C. for 60 sec to form a film having an average thickness of 200 nm. Accordingly, a film-attached substrate having been provided with the film thereon was obtained.

Evaluations

By using the compositions obtained and the film-attached substrates obtained, the following evaluations were each made according to the following procedures. The results of the evaluations are shown in Table 2 below.

Solvent Resistance

The film-attached substrate obtained as described above was immersed in cyclohexanone (at room temperature) for 1 min. Average thicknesses of the film before and after the immersion were measured. The average thickness of the film before the immersion was designated as $X_0$ and the average thickness of the film after the immersion was designated as $X_1$, and an absolute value of a numerical value determined according to $(X_1-X_0)\times100/X_0$ was calculated and designated as a rate of change in film thickness (%). The solvent resistance was evaluated to be: "A" (favorable) in a case in which the rate of change in film thickness was less than 1%; "B" (somewhat favorable) in a case in which the rate of change in film thickness was no less than 1% and less than 5%; and "C" (unfavorable) in a case in which the rate of change in film thickness was no less than 5%.

Flatness

Each of the compositions prepared as described above was applied by a spin-coating procedure using a spin coater ("CLEAN TRACK ACT-12" available from Tokyo Electron Limited), on a silicon substrate 1 provided with a trench pattern having a depth of 100 nm and a groove width of 10 μm formed thereon, as shown in FIG. 1. A rotational speed for the spin coating was the same as that in the case of forming the film having the average thickness of 200 nm in the "Film Formation" as above. Subsequently, by heating (baking) in an ambient air atmosphere, at a heating temperature (° C.) for a heating time period (sec) shown in Table 2 below, a film was formed having an average thickness of 200 nm at parts having no trench provided. Accordingly, a film-attached silicon substrate, the silicon substrate being covered by the film, was obtained.

A cross-sectional shape of the film-attached silicon substrate was observed by using a scanning electron microscope ("S-4800" available from Hitachi High-Technologies Corporation), and the difference (ΔFT) between a height at the center portion "b" of the trench pattern of the film and a height at a position "a" 5 μm away from the edge of the trench pattern, at which no trench pattern was provided, was defined as a marker of the flatness. The flatness was evaluated to be: "A" (favorable) in a case of ΔFT being less than 40 nm; "B" (somewhat favorable) in a case of ΔFT being no less than 40 nm and less than 60 nm; and "C" (unfavorable) in a case of ΔFT being no less than 60 nm. It is to be noted that the difference in heights shown in FIG. 1 is exaggerated.

Wet Peel Resistance

The composition prepared as described above was applied on a silicon wafer (substrate) with a spin coater. Next, by heating (baking) in an ambient air atmosphere at the heating temperature (° C.) for the heating time period (sec) shown in Table 2 below, a film having an average thickness of 150 nm was formed. Accordingly, a film-attached substrate having been provided with the film thereon was obtained. The film-attached substrate was immersed in alkaline hydrogen peroxide water (in a mix liquid (SC1) of 25% by mass aqueous ammonia solution/30% by mass aqueous hydrogen peroxide solution/water=1/2/40 (mass ratio), at 60 to 65° C.) for 5 min, and washed with water and dried. Average thicknesses of the film before and after the immersion were measured. The average thickness of the film before the immersion was designated as $T_0$ and the average thickness of the film after the immersion was designated as $T_1$, and an absolute value of a numerical value determined according to $(T_1-T_0)\times100/T_0$ was calculated and designated as a rate of change in film thickness (%). The wet peel resistance was evaluated to be: "A" (favorable) in a case in which the rate of change in film thickness was less than 5%; and "B" (unfavorable) in a case in which the rate of change of film thickness was no less than 5%.

Flexural Resistance

The composition prepared as described above was applied by a spin-coating procedure on a silicon substrate on which a thermally-oxidized film having an average thickness of 500 nm had been formed. A film-attached substrate, having been provided with the film thereon, having an average thickness of 200 nm was obtained by thereafter heating (baking) at 350° C. for 60 sec in an ambient air atmosphere. On the film-attached substrate thus obtained, a composition for silicon-containing film formation ("NFC SOG080" available from JSR Corporation) was applied by a spin-coating procedure and then heated (baked) at 200° C. for 60 sec in an ambient air atmosphere, followed by additional heating (baking) at 300° C. for 60 sec to form a silicon-containing film having an average thickness of 50 nm. Next, a resist composition for ArF ("AR1682J" available from JSR Corporation) was applied on the silicon-containing film by a spin-coating procedure and then heated (baked) at 130° C. for 60 sec in an ambient air atmosphere to form a resist film having an average thickness of 200 nm. Thereafter, the resist film was subjected to an exposure with an exposure dose altered through a 1:1 line-and-space mask pattern with a target size of 100 nm by using an ArF excimer laser lithography device available from Nikon Corporation (lens numerical aperture: 0.78; exposure wavelength: 193 nm), and then heated (baked) at 130° C. for 60 sec in an ambient air atmosphere. A development was carried out with a 2.38% by mass aqueous tetramethylammonium hydroxide (TMAH) solution at 25° C. for 1 min, followed by washing with water and drying. Accordingly, a line-and-space resist-patterned substrate with a pitch of 200 nm was obtained having a line width of the line pattern being from 30 nm to 100 nm.

Using the resist pattern as a mask, the silicon-containing film was etched with an etching apparatus ("TACTRAS" available from Tokyo Electron Limited) under a condition of $CF_4$=200 sccm, PRESS.=85 mT, HF RF (high-frequency power for plasma production)=500 W, LF RF (high-frequency power for bias)=0 W, DCS=−150 V, and RDC (proportion of gas center flow rate)=50% to give a substrate patterned on the silicon-containing film. Next, using the silicon-containing film pattern as a mask, the film was etched with the etching apparatus ("TACTRAS" available from Tokyo Electron Limited) under a condition of $O_2$=400 sccm, PRESS.=25 mT, HF RF (high-frequency power for plasma production)=400 W, LF RF (high-frequency power for bias)=0 W, DCS=0 V, and RDC (proportion of gas center flow rate)=50% to give the substrate patterned on the film. Using the film pattern as a mask, the thermally-oxidized film was etched with an etching apparatus ("TACTRAS" available from Tokyo Electron Limited) under a condition of $CF_4$=180 sccm, Ar=360 sccm, PRESS.=150 mT, HF RF (high-frequency power for plasma production)=1,000 W, LF RF (high-frequency power for bias)=1,000 W, DCS=−150 V, and RDC (proportion of gas center flow rate)=50%, for 60 sec.

Figure 2:
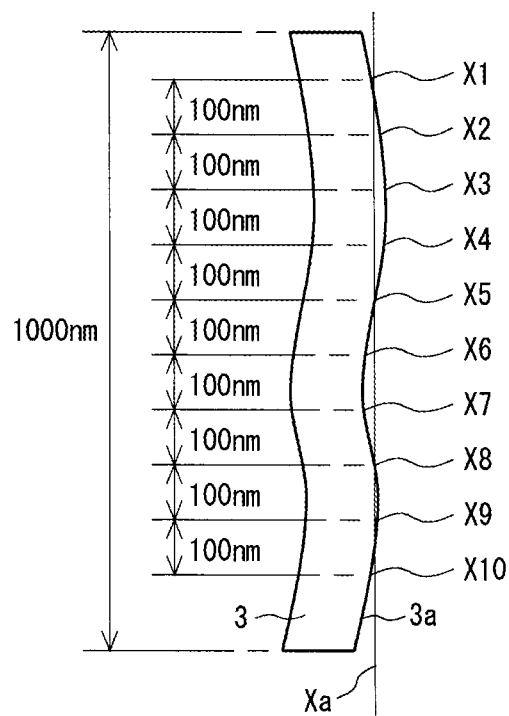
FIG. 2 is a schematic plan view for illustrating an evaluation method of flexural resistance.

Thereafter, a 250,000 times enlarged image of the configuration of the film pattern with each line width was obtained by a scanning electron microscope ("CG-4000" available from Hitachi High-Technologies Corporation), and an image processing thereof was executed. Accordingly, as shown in FIG. 2, LER (line-edge roughness) was determined on a side lateral face 3a of a film pattern 3 (line pattern) with a length of 1,000 nm in the configuration thus observed, in terms of a 3 Sigma value derived by triplicating a standard deviation calculated from: positions Xn (n=1 to 10) in a line width direction measured at ten points with intervals of 100 nm; and a position Xa corresponding to an average of these positions in the line width direction. LER, indicating a degree of bending of the film pattern, increases as the line width of the film pattern decreases. On the basis of the line width of the film pattern that results in LER of 5.5 nm, the flexural resistance was evaluated to be: "A" (favorable) in a case in which this line width was less than 40.0 nm; "B" (somewhat favorable) in a case in which this line width was no less than 40.0 nm and less than 45.0 nm; and "C" ("unfavorable") in a case in which this line width was no less than 45.0 nm. It is to be noted that the bending feature of the film pattern shown in FIG. 2 is exaggeratedly illustrated.

TABLE 2

| | Composition | Heating temperature/ heating time in film formation (° C./sec) | Solvent resistance | Flatness | Wet peel resistance | Flexural resistance |
|---|---|---|---|---|---|---|
| Example 2-1 | J-1 | 350/60 | A | A | A | A |
| Example 2-2 | J-2 | 350/60 | A | A | A | A |
| Example 2-3 | J-3 | 350/60 | A | A | A | A |
| Example 2-4 | J-4 | 350/60 | A | A | A | A |
| Example 2-5 | J-5 | 350/60 | A | A | A | A |
| Example 2-6 | J-6 | 350/60 | A | A | A | A |
| Example 2-7 | J-7 | 350/60 | A | A | A | A |
| Example 2-8 | J-8 | 350/60 | A | A | A | B |
| Example 2-9 | J-9 | 350/60 | A | A | A | A |
| Example 2-10 | J-10 | 350/60 | A | B | A | B |
| Example 2-11 | J-11 | 350/60 | A | A | A | A |
| Comparative Example 2-1 | CJ-1 | 350/60 | A | C | B | C |

As is revealed from the results shown in Table 2, the compositions and the film-attached substrates of the Examples were superior in flatness, wet peel resistance, and flexural resistance of the pattern, with solvent resistance being maintained. To the contrary, the compositions and the film-attached substrates of the Comparative Examples were superior in solvent resistance; however, the flatness and the flexural resistance of the pattern were inferior, with wet peel resistance also being poor.

The composition of the embodiment of the present invention enables formation of a film that is superior in flatness, wet peel resistance, and flexural resistance of a pattern, with solvent resistance being maintained. The film of the embodiment of the present invention is superior in flatness, wet peel resistance, and flexural resistance of the pattern, with solvent resistance being maintained. The film-forming method of the embodiment of the present invention enable formation of a film that is superior in flatness, wet peel resistance, and flexural resistance of a pattern, with solvent resistance being maintained. The patterned substrate-producing method of the embodiment of the present invention enables a favorable patterned substrate to be obtained by using a superior film formed as described above. Therefore, these can be suitably used for manufacture, etc., of semiconductor devices in which further progress of microfabrication is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A composition comprising:
a compound which is a polymer or non-polymeric compound; and
a solvent,
wherein the polymer comprises three or more groups each independently represented by formula (1), the non-polymeric compound is represented by formula (2), and the compound has a molecular weight of no less than 200 and no greater than 2,000, and has a percentage content of carbon atoms of no less than 40% by mass:

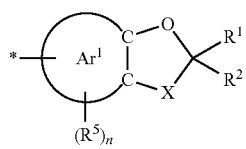

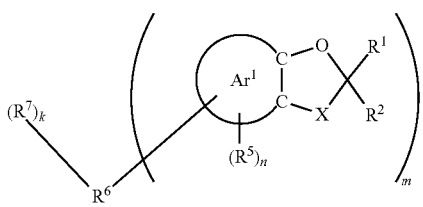

wherein, in the formula (1) and the formula (2):
$R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;
$Ar^1$ represents a group obtained by removing (n+3) hydrogen atoms from an arene or heteroarene having 6 to 20 ring atoms;
X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond; and n is an integer of 0 to 9, wherein
in a case in which n is 1, $R^5$ represents a hydroxy group, a halogen atom, a nitro group or a monovalent organic group having 1 to 20 carbon atoms, and
in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond,
in the formula (1): * denotes a binding site to a part other than the group represented by the formula (1) in the compound, and
in the formula (2): $R^6$ represents a hydrocarbon group having 1 to 60 carbon atoms and having a valency of (m+k), a group (β) that comprises a divalent hetero atom-containing group between two adjacent carbon atoms of the hydrocarbon group, or a group obtained by substituting a part or all of hydrogen atoms included in the hydrocarbon group or the group (β) with a monovalent hetero atom-containing group;
$R^7$ represents a monovalent organic group having 1 to 20 carbon atoms;
m is an integer of 3 to 10; and
k is an integer of 0 to 9, wherein (m+k) is no greater than 10, and wherein a plurality of $R^1$s are identical or different from each other, a plurality of $R^2$s are identical or different from each other, a plurality of Xs are identical or different from each other, a plurality of $Ar^1$s are identical or different from each other and a plurality of n's are identical or different from each other, and in a case in which k is no less than 2, a plurality of $R^7$s are identical or different from each other,
wherein when the compound is a polymer, the polymer is at least one selected from the group consisting of a phenol resin, a naphthol resin, a fluorene resin, an aromatic ring-containing vinyl-based resin, an acenaphthylene resin, an indene resin, an arylene resin, a triazine resin, a pyrene resin, a fullerene resin, and a calixarene resin, and
wherein a content of the compound in the composition relative to a total mass of a solid component of the composition is 50% by mass or more.

2. The composition according to claim 1, wherein the arene in the group represented by $Ar^1$ in the formula (1) or the formula (2) is benzene or naphthalene.

3. The composition according to claim 1, wherein X in the formula (1) or the formula (2) represents an oxygen atom.

4. The composition according to claim 1, wherein a percentage content of hydrogen atoms in the compound is no greater than 6.5% by mass.

5. A film formed from the composition according to claim 1.

6. The composition according to claim 1, wherein in the formula (2), $R^6$ is represented by at least one formula selected from the group consisting of formula (1-1), formula (1-2), formula (1-3), formula (1-4), formula (1-5), and formula (1-6):

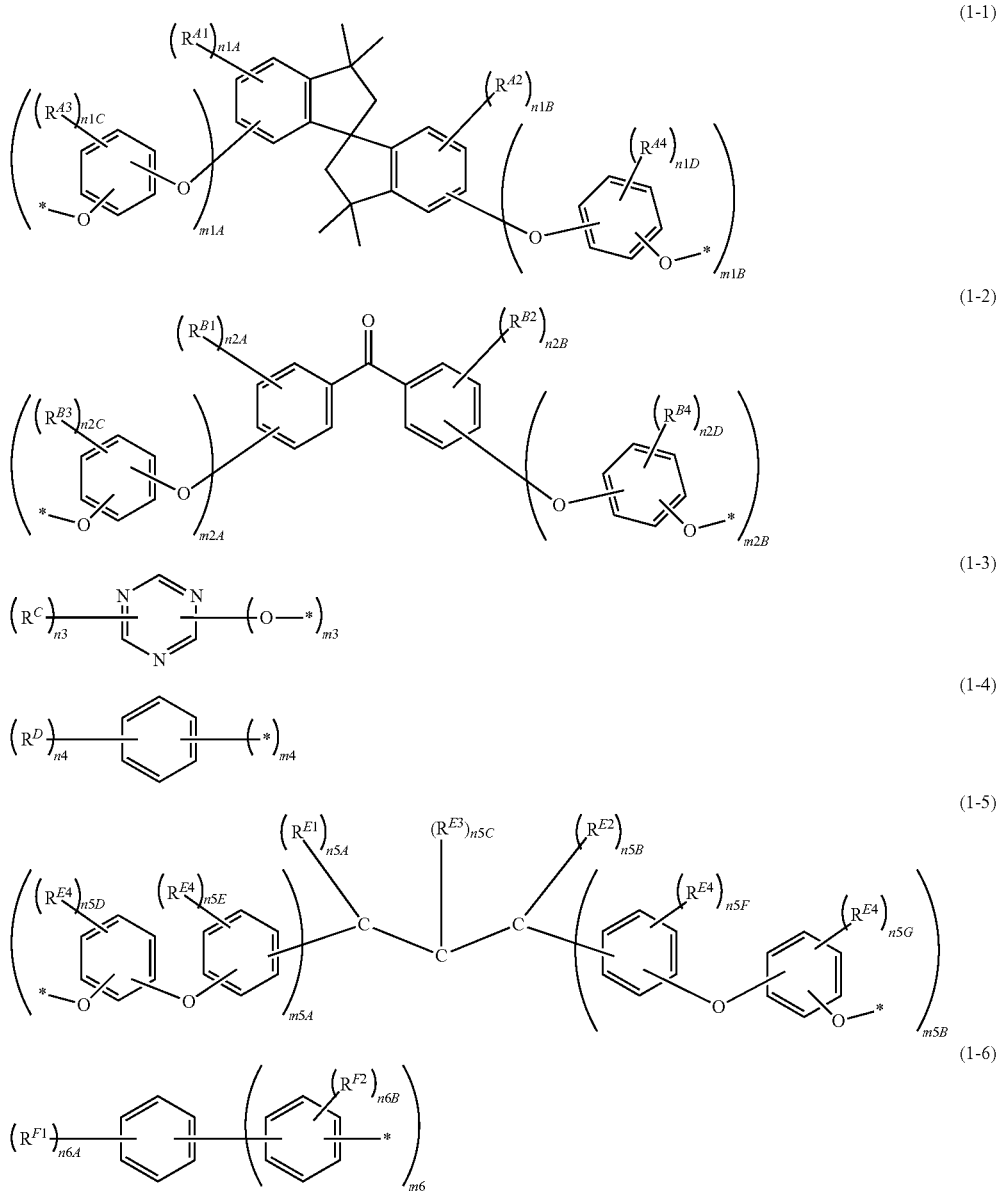

wherein, in the formulae (1-1) to (1-6): * denotes a site that bonds to a carbon atom on an aromatic ring in $Ar^1$ in the formula (2), in the formula (1-1): $R^{A1}$ to $R^{A4}$ each represent a hydroxy group, a halogen atom, a nitro group or a monovalent organic group having 1 to 20 carbon atoms; n1A and n1B are each an integer of 0 to 3; n1C and n1D are each an integer of 0 to 4; and m1A and m1B are each an integer of 1 to 4, wherein a sum of m1A and m1B is 3 or more, in a case in which n1A is no less than 2, a plurality of $R^{A1}$s are identical or different from each other, in a case in which n1B is no less than 2, a plurality of $R^{A2}$s are identical or different from each other, in a case in which n1C is no less than 2, a plurality of $R^{A3}$s are identical or different from each other, and in a case in which n1D is no less than 2, a plurality of $R^{A4}$s are identical or different from each other, and wherein (n1A+m1A)≤4, and (n1B+m1B)≤4;

in the formula (1-2): $R^{B1}$ to $R^{B4}$ each represent a hydroxy group, a halogen atom, a nitro group or a monovalent organic group having 1 to 20 carbon atoms; n2A, n2B, n2C and n2D are each an integer of 0 to 4; and m2A and m2B are each an integer of 1 to 5, wherein a sum of m2A and m2B is 3 or more, in a case in which n2A is no less than 2, a plurality of $R^{B1}$s are identical or different from each other, in a case in which n2B is no less than 2, a plurality of $R^{B2}$s are identical or different from each other, in a case in which n2C is no less than 2, a plurality of $R^{B3}$s are identical or different from each other, and in a case in which n2D is no less than 2, a plurality of $R^{B4}$s are identical or different from each other, and wherein (n2A+m2A)≤5, and (n2B+m2B)≤5;

in the formula (1-3): n3 is 0; and m3 is 3;

in the formula (1-4): $R^D$ represents a hydroxy group, a halogen atom, a nitro group or a monovalent organic group having 1 to 20 carbon atoms; n4 is an integer of 0 to 3; and m4 is an integer of 3 to 6, wherein in a case in which n4 is no less than 2, a plurality of $R^D$s are identical or different from each other, and wherein $(n4+m4) \leq 6$;

in the formula (1-5): $R^{E1}$ to $R^{E7}$ each represent a hydroxy group, a halogen atom, a nitro group or a monovalent organic group having 1 to 20 carbon atoms; n5A, n5B and n5C are each an integer of 0 to 2; n5D, n5E, n5F and n5G are each an integer of 0 to 4; and m5A and m5B are each an integer of 1 or 2, wherein a sum of m5A and m5B is 3 or more, in a case in which n5A is 2, a plurality of $R^{E1}$s are identical or different from each other, in a case in which n5B is 2, a plurality of $R^{E2}$s are identical or different from each other, in a case in which n5C is 2, a plurality of $R^{E3}$s are identical or different from each other, in a case in which n5D is no less than 2, a plurality of $R^{E4}$s are identical or different from each other, in a case in which n5E is no less than 2, a plurality of $R^{E5}$s are identical or different from each other, in a case in which n5F is no less than 2, a plurality of $R^{E6}$s are identical or different from each other, and in a case in which n5G is no less than 2, a plurality of $R^{E'}$s are identical or different from each other, and wherein $(n5A+m5A) \leq 3$, and $(n5B+m5B) \leq 3$; and in the formula (1-6): $R^{F1}$ and $R^{F2}$ each represent a hydroxy group, a halogen atom, a nitro group or a monovalent organic group having 1 to 20 carbon atoms; n6A is an integer of 0 to 3; n6B is an integer of 0 to 4; and m6 is an integer of 3 to 6, wherein in a case in which n6A is no less than 2, a plurality of $R^{F1}$s are identical or different from each other, and in a case in which n6B is no less than 2, a plurality of $R^{F2}$s are identical or different from each other, and wherein $(n6A+m6) \leq 6$.

7. The composition according to claim 1, wherein the compound is represented by at least one formula selected from the group consisting of formula (i-1), formula (i-2), formula (i-3), formula (i-4), formula (i-5), formula (i-6), and formula (i-7):

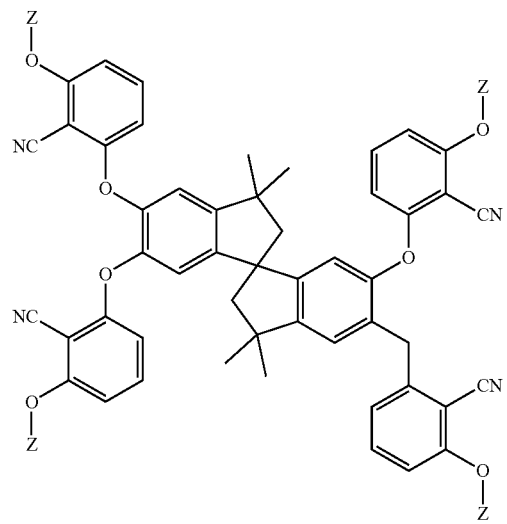
(i-1)

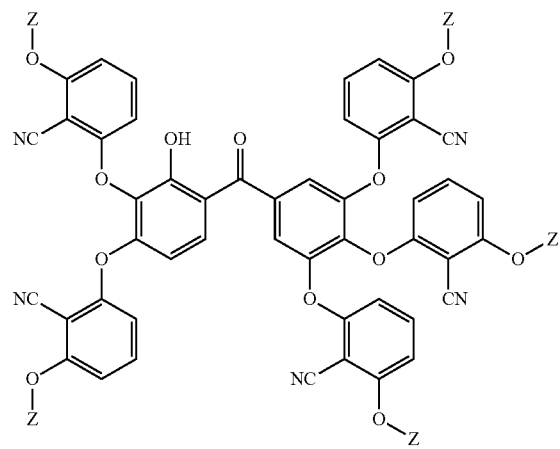
(i-2)

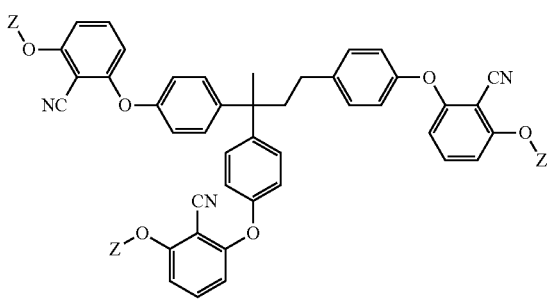
(i-3)

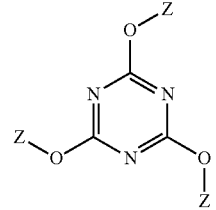
(i-4)

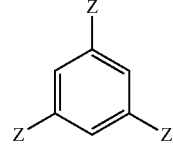
(i-5)

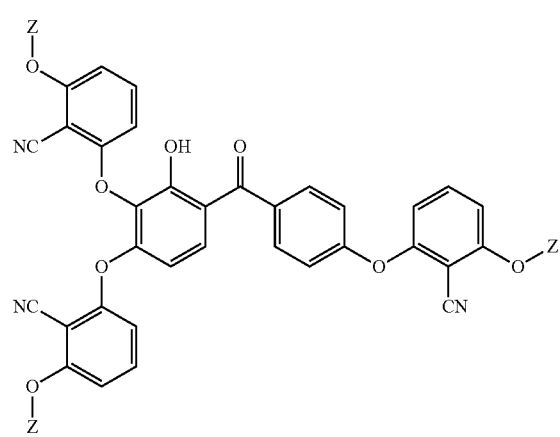
(i-6)

-continued (i-7)

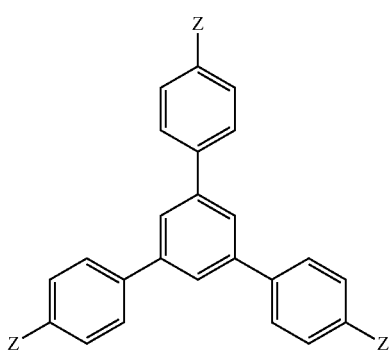

wherein each Z is independently represented by formula (1).

8. The composition according to claim 1, wherein the content of the compound in the composition relative to the total mass of the solid component of the composition is 70% by mass or more.

9. The composition according to claim 1, wherein the content of the compound in the composition relative to the total mass of the solid component of the composition is 85% by mass or more.

10. The film-forming method comprising:
applying a composition directly or indirectly on at least an upper face side of a substrate to form a coating film; and
heating the coating film at a temperature of no less than 300° C.,
wherein the composition comprises:
a compound comprising a group represented by formula (1), the compound having a molecular weight of no less than 200 and no greater than 2,000, and having a percentage content of carbon atoms of no less than 40% by mass; and
a solvent,

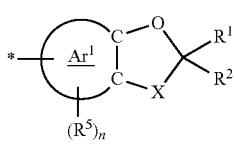

(1)

wherein, in the formula (1),
$R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;
$Ar^1$ represents a group obtained by removing (n+3) hydrogen atoms from an arene or heteroarene having 6 to 20 ring atoms;
X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond;
n is an integer of 0 to 9, wherein
in a case in which n is 1, $R^5$ represents a hydroxy group, a halogen atom, a nitro group or a monovalent organic group having 1 to 20 carbon atoms, and
in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and
* denotes a binding site to a part other than the group represented by the formula (1) in the compound, and
wherein the compound is a non-polymeric compound or a polymer, and when the compound is a polymer, the polymer is at least one selected from the group consisting of a phenol resin, a naphthol resin, a fluorene resin, an aromatic ring-containing vinyl-based resin, an acenaphthylene resin, an indene resin, an arylene resin, a triazine resin, a pyrene resin, a fullerene resin, and a calixarene resin.

11. A patterned substrate-producing method comprising:
applying a composition directly or indirectly on at least an upper face side of a substrate to form a coating film;
heating the coating film to form a film;
forming a silicon-containing film on an upper face side of the film formed by the heating; and
removing the silicon-containing film with a basic liquid, the composition comprising:
a compound comprising a group represented by formula (1), the compound having a molecular weight of no less than 200 and no greater than 2,000, and having a percentage content of carbon atoms of no less than 40% by mass; and
a solvent,

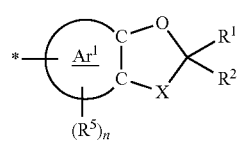

(1)

wherein, in the formula (1),
$R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;
$Ar^1$ represents a group obtained by removing (n+3) hydrogen atoms from an arene or heteroarene having 6 to 20 ring atoms;
X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond;

n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and

* denotes a binding site to a part other than the group represented by the formula (1) in the compound.

12. The patterned substrate-producing method according to claim 11, wherein the compound comprises two or more groups represented by the formula (1).

13. The patterned substrate-producing method according to claim 11, wherein the arene represented by $Ar^1$ in the formula (1) is benzene or naphthalene.

14. The patterned substrate-producing method according to claim 11, wherein X in the formula (1) represents an oxygen atom.

15. A patterned substrate-producing method comprising:
applying a composition directly or indirectly on at least an upper face side of a substrate to form a coating film;
heating the coating film to form a film;
forming a silicon-containing film on an upper face side of the film formed by the heating;
forming a resist pattern on an upper face sided of the silicon-containing film; and
etching the substrate using the resist pattern as a mask,
the composition comprising:
a compound comprising a group represented by formula (1), the compound having a molecular weight of no less than 200 and no greater than 2,000, and having a percentage content of carbon atoms of no less than 40% by mass; and
a solvent,

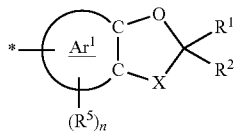
(1)

wherein, in the formula (1), $R^1$ and $R^2$ each independently represent a hydrogen atom, a fluorine atom, a monovalent hydrocarbon group having 1 to 20 carbon atoms or a monovalent fluorinated hydrocarbon group having 1 to 20 carbon atoms, or $R^1$ and $R^2$ taken together represent a part of an alicyclic structure having 3 to 20 ring atoms constituted together with the carbon atom to which $R^1$ and $R^2$ bond;

$Ar^1$ represents a group obtained by removing (n+3) hydrogen atoms from an arene or heteroarene having 6 to 20 ring atoms;

X represents an oxygen atom, —$CR^3R^4$—, —$CR^3R^4$—O— or —O—$CR^3R^4$—, wherein $R^3$ and $R^4$ each independently represent a hydrogen atom, a fluorine atom, a monovalent hydrocarbon group having 1 to 20 carbon atoms or a monovalent fluorinated hydrocarbon group having 1 to 20 carbon atoms, or $R^3$ and $R^4$ taken together represent a part of an alicyclic structure having 3 to 20 ring atoms constituted together with the carbon atom to which $R^3$ and $R^4$ bond;

n is an integer of 0 to 9, wherein in a case in which n is 1, $R^5$ represents a hydroxy group, a halogen atom, a nitro group or a monovalent organic group having 1 to 20 carbon atoms, and in a case in which n is no less than 2, a plurality of $R^5$s are identical or different from each other, and each $R^5$ independently represents a hydroxy group, a halogen atom, a nitro group or a monovalent organic group having 1 to 20 carbon atoms, or two or more of the plurality of $R^5$s taken together represent a part of a ring structure having 4 to 20 ring atoms constituted together with an atom chain to which the two or more of the plurality of $R^5$s bond, and

* denotes a binding site to a part other than the group represented by the formula (1) in the compound.

16. The patterned substrate-producing method according to claim 15, wherein the compound comprises two or more groups represented by the formula (1).

17. The patterned substrate-producing method according to claim 15, wherein the arene represented by $Ar^1$ in the formula (1) is benzene or naphthalene.

18. The patterned substrate-producing method according to claim 15, wherein X in the formula (1) represents an oxygen atom.

* * * * *

UNITED STATES PATENT AND TRADEMARK OFFICE
CERTIFICATE OF CORRECTION

PATENT NO. : 11,667,620 B2
APPLICATION NO. : 16/809740
DATED : June 6, 2023
INVENTOR(S) : Nakatsu et al.

It is certified that error appears in the above-identified patent and that said Letters Patent is hereby corrected as shown below:

In the Claims

Claim 6, Column 43, formula (1-5) should appear as follows:

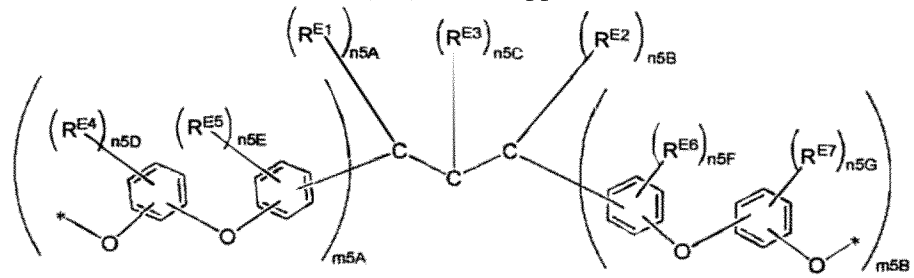

Claim 6, Column 45, Line 24, "$R^E$'s" should read as --$R^{E7}$s--

Claim 7, Column 45, formula (i-1) should appear as follows:

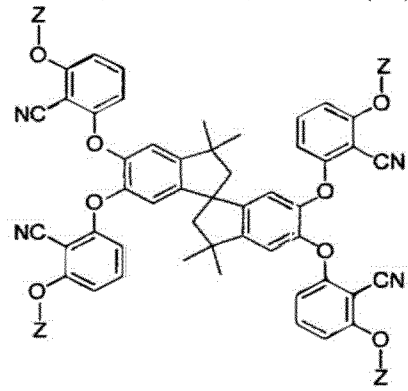

Signed and Sealed this
Third Day of December, 2024

*Katherine Kelly Vidal*

Katherine Kelly Vidal
*Director of the United States Patent and Trademark Office*